(12) United States Patent
Oliner et al.

(10) Patent No.: US 6,258,536 B1
(45) Date of Patent: Jul. 10, 2001

(54) EXPRESSION MONITORING OF DOWNSTREAM GENES IN THE BRCA1 PATHWAY

(76) Inventors: Jonathan Oliner, 173 Sierra Vista Ave., Unit 22, Mountain View, CA (US) 94043; Fred Christians, 1444 Arbor Ave., Los Altos, CA (US) 94024; Vivi Truong, 7082 Kindra Hill Dr., San Jose, CA (US) 95120; Daniel Haber, 34 Monadonck Rd., Chestnut Hill, MA (US) 02467; James Bean, 9 Heath Rd., Arlington, MA (US) 02474; David Miklos, 61 Oriole St., W. Roxbury, MA (US) 02132; Denis Paul Harkin, 9 Knockhill Park, Belfast BT5 6HX, Northern Ireland (GB)

(*) Notice: Subject to any disclaimer, the term of this patent is extended or adjusted under 35 U.S.C. 154(b) by 0 days.

(21) Appl. No.: 09/203,677

(22) Filed: Dec. 1, 1998

(51) Int. Cl.[7] .................... C12Q 1/68; G01N 33/53; C12P 21/06; A61K 49/00; C07H 21/04

(52) U.S. Cl. .................... 435/6; 435/6; 435/7.1; 435/69.1; 424/9; 536/23.5

(58) Field of Search .................... 435/69.1, 7.1, 435/6; 424/9; 536/23.5

(56) References Cited

U.S. PATENT DOCUMENTS

| 5,174,986 | * | 12/1992 | Berns | 424/9 |
|---|---|---|---|---|
| 5,248,591 | * | 9/1993 | Puente | 435/7.1 |
| 5,700,637 | | 12/1997 | Southern | 435/6 |
| 5,747,282 | * | 5/1998 | Skolnick et al. | 435/69.1 |
| 5,981,218 | * | 11/1999 | Rio et al. | 435/69.1 |

FOREIGN PATENT DOCUMENTS

89/10977   11/1989   (WO).

OTHER PUBLICATIONS

Derisi et al., "Use of a cDNA microarray to analyse gene expression patterns in human cancer", Nature Genetics, vol. 14, pp. 457–460, Dec. 1996.*

Galang et al., "Oncogenic Neu/ErbB–2 Increases Ets, AP–1, and NF–kB–dependent Gene Expression, and Inhibiting Ets Activation Blocks Neu–mediated Cellular Transformation", The Journal of Biological Chemistry, vol. 271 (14), pp. 7992–7998, Apr. 6, 1996.*

Honkoop et al. "Prognostic role of clinical, pathological and biological characteristics in patients with locally advanced breast cancer" British Journal of Cancer (1998) 77 (4), 621–626.

Tsitsiloni et al. "Expression of α–thymosins in human tissues in normal and abnormal growth" Proc. Natl. Acad. Sci. USA vol. 90 pp. 9504–9507 Oct. 1993.

Elizabeth M. Jarvis et al. "Loss of Nuclear BRCA1 Expression in Breast Cancer is Associated with a Highly Proliferative Tumor Phenotype" Cancer Genet Cytogenet 101:109–115 (1998).

Alvaro N.A. Monteiro et al. "Evidence for a transcriptional activation function of BRCA1 C–terminal region" Proc. Natl. Acad. Sci. USA, vol. 95, pp. 13595–13599 Nov. 1996.

(List continued on next page.)

Primary Examiner—Jeffrey Fredman
Assistant Examiner—Arun K. Chakrabarti
(74) Attorney, Agent, or Firm—Banner & Witcoff, Ltd.

(57) ABSTRACT

Analysis of the genes whose expression is affected by BRCA1 has identified a set of genes, each of which is up- or down-regulated by BRCA1. Each of these genes, alone or in groups, can be used to determine the mutational status of a BRCA1 gene, to determine whether a particular allelic variant affects BRCA1 function, to diagnose neoplasia, and to help identify candidate drugs which may be useful as anti-neoplastic agents.

32 Claims, 13 Drawing Sheets

(3 of 13 Drawing Sheet(s) Filed in Color)

OTHER PUBLICATIONS

Yoshio Miki et al. "A Strong Candidate for the Breast and Ovarian Cancer Suceptibility Gene BRCA1" Science, vol. 266, Oct. 7, 1994 pp. 66–71.

Mark S. Chapman et al., Nature, vol. 382, Aug. 22, 1996 "Transcriptional activation by BRCA1" pp. 678–679.

Ralph Scully et al. "Association of BRCA1 with Rad51 in Mitotic and Meiotic Cells" Cell, vol. 88, 265–275 Jan. 24, 1997.

* cited by examiner

FIG. 6A

| Accession no. | Description | Array Hybridization Signal | | | Fold induction by northern |
|---|---|---|---|---|---|
| | | 0 | 6 | 12 | 24 HRS. | |
| U14680 | BRCA1 | 23 | 822 | 1117 | 1770 | 60 |
| M60974 | GADD45 | 93 | 371 | 295 | 914 | 35 |
| X52541 | EGR1 | 31 | 106 | 286 | 705 | 10 |
| M92843 | Tristetraproline (TTP) | -200 | 64 | 260 | 357 | 5 |
| R40776 | Gem GTPase | 346 | 742 | 805 | 835 | 5 |
| M91585 | Br140 | 24 | 60 | 319 | 230 | 4 |
| R12810 | unidentified cDNA | -19 | 160 | -44 | 249 | 4 |
| M58460 | PM-scl 75 | 18 | 87 | 94 | 146 | 3 |
| L19871 | ATF3 | 24 | 26 | 89 | 219 | 3 |
| L04510 | ARD1 | 124 | 159 | 246 | 464 | 3 |
| T40949 | Hepatic Leukemia Factor | -57 | -26 | 129 | 246 | 3 |
| M30704 | Amphiregulin | -18 | 29 | 41 | 123 | 3 |
| H83392 | TR3 Orphan Receptor (NAK1) | -109 | 49 | 48 | 78 | 3 |
| R70479 | TNFα-inducible gene A20 | -12 | 57 | 106 | 169 | 2 |
| U09278 | Fibroblast Activating Protein α | 1 | 30 | 47 | 91 | 2 |
| H44764 | IL4 Receptor α | -27 | 81 | 87 | 147 | 2 |
| M62831 | ETR101 | 381 | 696 | 845 | 1202 | 2 |
| R41997 | EST | -1.5 | 12 | 60 | 93 | 2 |
| H81220 | EST | -24 | -4 | 14 | 49 | 2 |
| D29956 | KIAA0055 | 14 | 23 | 47 | 67 | 2 |

EXPRESSION MONITORING OF DOWNSTREAM GENES IN THE BRCA1 PATHWAY

BACKGROUND OF THE INVENTION

Many biological functions are accomplished by altering the expression of various genes through transcriptional (e.g. through control of initiation, provision of RNA precursors, RNA processing, etc.) and/or translational control. For example, fundamental biological processes such as cell cycle, cell differentiation and cell death, are often characterized by variations in the expression levels of groups of genes.

Gene expression is also associated with pathogenesis. For example, the lack of sufficient expression of functional tumor suppressor genes and/or the over expression of oncogene/protooncogenes could lead to tumorigenesis (Marshall, Cell, 64: 313–326 (1991); Weinberg, Science, 254: 1138–1146 (1991), incorporated herein by reference for all purposes). Thus, changes in the expression levels of particular genes (e.g. oncogenes or tumor suppressors) serve as signposts for the presence and progression of various diseases.

BRCA1 encodes a tumor suppressor gene that is mutated in the germline of women with genetic predisposition to breast and ovarian cancer. Germline mutations are found in approximately half of breast-ovarian cancer pedigrees and in ~10% of women with early onset of breast cancer, irrespective of family history. Most mutations result in premature protein truncation and as predicted heterozygous germline mutations show reduction to homozygosity (LOH) within tumor specimens. However, somatic inactivation of BRCA1 is uncommon in sporadic breast cancer, pointing to potentially distinct genetic mechanisms.

Functional properties of BRCA1 have been inferred from its pattern of subnuclear localization. During S phase, endogenous BRCA1 is present within nuclear dots that are colocalized with RAD51, the mammalian homolog of bacterial recA, involved in homologous recombination and the repair of double-strand breaks in DNA following ionizing radiation. BRCA1 and RAD51 are also colocalized during meiosis, a process that involves programmed homologous recombination and in which both BRCA1 and RAD51 proteins are found along unsynapsed chromosomes. BRCA1 is also colocalized with the product of the second breast cancer predisposition gene, BRCA2, whose role in the maintenance of chromosomal integrity is suggested by analysis of mice with a partial loss of function phenotype. Consistent with a potential role in the repair of DNA damage, treatment of cultured cells with ionizing radiation leads to the hyperphosphorylation of BRCA1 and the disappearance of BRCA1 nuclear dots.

In addition to its potential role in homologous recombination, BRCA1 demonstrates properties of a transcription factor or cofactor. Protein purification studies have shown that it coelutes with the RNA polymerase II holoenzyme complex and interacts with RNA helicase, consistent with its involvement in some aspect of transcriptional regulation The C-terminal domain of BRCA1 mediates transcriptional activation when fused to a heterologous DNA binding domain, and a potential target promoter is that of the cyclin-dependent kinase inhibitor p21. In transient transfection assays, BRCA1 mediates transcriptional activation of the p21 promoter, through a site that is distinct from that implicated in its regulation by p53. However, BRCA1 has also been shown to enhance p53-mediated activation of the p21 promoter in transient transfection assays, suggesting that this effect may have both p53 dependent and independent components.

Recently, a defect in transcription-coupled repair of oxidative, but not UV-induced DNA damage has been demonstrated in mouse embryo fibroblasts with attenuated BRCA1 function. BRCA1 has therefore, been implicated in three distinct functional pathways, namely RAD51-dependent homologous recombination, transcriptional activation of p21, and transcription-coupled repair of oxidative DNA damage. The physiological significance of these properties and their implications for the function of BRCA1 as a tumor suppressor gene remain to be defined.

Definitive studies of BRCA1 function have been hampered by the absence of BRCA1-null cell lines and the difficulty in achieving stable expression of a transfected full length cDNA. Cells stably transfected with a truncated BRCA1 construct lacking the large central exon 11 undergo accelerated apoptosis following serum withdrawal, while retroviral infection using a 5' truncated BRCA1 construct encoding a protein of 190 kD that lacks the N terminal ring domain, inhibits colony formation. Analysis of thymidine incorporation in transiently transfected cells has suggested a block in S phase entry, associated with induction of p21.

Thus there is a need in the art for information on the functional properties of BRCA1 and its effect on endogenous target genes. Because of the important role of BRCA1 in inherited breast and ovarian cancers, such information can be useful diagnostically as well as in developing new generations of therapeutic agents.

SUMMARY OF THE INVENTION

It is an object of the invention to provide a method for detecting a BRCA1 gene functional mutation in target cells.

It is another object of the invention to provide an in-cell functional assay for a BRCA1 sequence alteration.

It is still another object of the invention to provide a computer assisted method for detecting a mutation in a target BRCA1 gene.

It is yet another object of the invention to provide a method of diagnosing neoplasia.

It is another object of the invention to provide a method of identifying potential anti-cancer drugs.

These objects of the invention are provided by one or more of the embodiments described below. In one embodiment of the invention, a method for detecting a BRCA1 gene functional mutation in target cells is provided. The method comprises detecting expression of a plurality of down-stream genes of BRCA1 in a sample of (a) target cells, and (b) reference cells having a wild-type BRCA1 gene. The reference cells are otherwise substantially similar to the target cells. The down-stream genes are up- or down-regulated by the wild-type BRCA1 gene. The expression of the down-stream genes in the target cells and the reference cells are compared. A difference in the expression between the target cells and reference cells suggests a BRCA1 functional mutation in the target cells.

According to another embodiment of the invention, an in-cell functional assay for a BRCA1 sequence alteration is provided. The assay comprises detecting expression of a plurality of BRCA1 down-stream genes in a target sample from target cells having a BRCA1 sequence alteration and in a reference sample from reference cells having a wild-type BRCA1 gene. The reference cells are otherwise substantially similar to the target cells. The down-stream genes are up- or down-regulated by wild-type BRCA1 gene. The expression in the target sample is compared to the expression in the reference sample A difference in the expression between the two samples suggests that the BRCA1 sequence alteration affects the biological function of BRCA1.

According to still another aspect of the invention, a method is provided for detecting a mutation in a target BRCA1 gene using a computer. Wild-type expression data of a plurality of down-stream genes in a wild-type sample containing a wild-type BRCA1 gene is input into a computer. The down-stream genes are transcriptionally regulated by the wild-type BRCA1 gene. Target expression data of the plurality of down-stream genes in a target sample containing the target BRCA1 gene is also input into the computer. The target and wild-type expresssion data are compared by the computer to determine differences. Differences suggest a mutation in the target BRCA1 gene.

In yet another embodiment of the invention a method of diagnosing neoplasia of a test cell is provided. A transcription indicator of a test cell is hybridized to a set of nucleic acid probes. The transcription indicator is selected from the group consisting of mRNA, cDNA and cRNA. The set of nucleic acid probes comprises a plurality of nucleic acid molecules each of which is a portion of a gene which is activated by or repressed by BRCA1. Amounts of transcription indicator which hybridize to each of the set of nucleic acid probes are determined. A test cell is identified as neoplastic if (1) hybridization of the transcription indicator of the test cell to a probe which is a BRCA1-activated gene is lower than hybridization using a transcription indicator from a normal cell, or (2) hybridization of the transcription indicator of the test cell to a probe which a BRCA1-repressed gene is higher than hybridization using a transcription indicator from a normal cell.

In another embodiment of the invention, potential anti-cancer drugs are identified. A test compound is contacted with a human cell. Expression of a plurality of BRCA1 regulated genes is monitored. A test compound is identified as a potential anti-cancer drug if it increases expression of a BRCA1 up-regulated gene or decreases expression of a BRCA1 down-regulated gene in the human cell.

In still another aspect of the invention a method is provided for detecting a BRCA1 gene functional mutation in target cells. Expression is detected of a down-stream gene of BRCA1 in a sample of (a) target cells, and (b) reference cells having a wild-type BRCA1 gene. The reference cells are otherwise substantially similar to the target cells. The down-stream gene is selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α. The expression of the down-stream genes in the target cells and the reference cells are compared. A difference in the expression between the target cells and reference cells suggests a BRCA1 functional mutation in the target cells.

In still another embodiment of the invention an in-cell functional assay for a BRCA1 sequence alteration is provided. Expression is detected of a down-stream BRCA1-regulated gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α, in a target sample from target cells having a BRCA1 sequence alteration and in a reference sample from reference cells having a wild-type BRCA1 gene. The reference cells are otherwise substantially similar to the target cells. The expression in the target sample is compared to the expression in the reference sample. A difference in the expression between the two samples suggests that the BRCA1 sequence alteration affects the biological function of BRCA1.

According to another aspect of the invention, a method is provided for detecting a mutation in a target BRCA1 gene using a computer. Wild-type expression data of a down-stream gene in a wild-type sample containing a wild-type BRCA1 gene is input into the computer. The down-stream gene is transcriptionally regulated by the wild-type BRCA1 gene. The down-stream gene is selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α. Target expression data of the down-stream gene in a target sample containing the target BRCA1 gene is also input into the computer. The target and wild-type expresssion data are compared to determine differences. Such differences suggest a mutation in the target BRCA1 gene.

Another embodiment of the invention provides a method of diagnosing neoplasia of a test cell. A transcription indicator of a test cell is hybridized to a nucleic acid probe. The transcription indicator is selected from the group consisting of mRNA, cDNA and cRNA. The nucleic acid probe comprises a nucleic acid molecule which is a portion of a gene which is activated by or repressed by BRCA1. The gene is selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α. Amounts of transcription indicator which hybridize to the nucleic acid probe are detected. A test cell is identified as neoplastic if (1) hybridization of the transcription indicator of the test cell to the probe is lower than hybridization using a transcription indicator from a normal cell, or (2) hybridization of the transcription indicator of the test cell to the probe is higher than hybridization using a transcription indicator from a normal cell.

Another embodiment of the invention provides a method of identifying anti-cancer drugs. According to the method, a test compound is contacted with a human cell. Expression is monitored of a BRCA1-downstream gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α. A test compound is identified as a potential anti-cancer drug if it increases expression of a BRCA1 up-regulated gene or decreases expression of a BRCA1 down-regulated gene in the human cell.

According to another embodiment of the invention, a method of diagnosing neoplasia of a test cell is provided. Expression is detected in a test cell of a plurality of genes which are activated by or repressed by BRCA1. A test cell is identified as neoplastic if (1) expression of at least one of said BRCA1-activated genes is lower in the test cell than expression in a normal cell, or (2) expression of at least one of said BRCA1-repressed genes is higher than expression in a normal cell.

In yet another embodiment of the invention a method is provided for diagnosing neoplasia of a test cell. Expression is detected in a test cell of a gene which is activated by or repressed by BRCA1. The gene is selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α. A test cell is identified as neoplastic if (1) expression of a BRCA1-activated gene in the test cell is lower than expression of the gene in a normal cell, or (2) expression of a BRCA1-repressed gene in the test cell is higher than expression in a normal cell.

This invention thus provides the art with methods useful for cancer related analysis, diagnosis and research. In some of its specific applications, this invention provides methods for detecting mutations of upstream BRCA1 genes by monitoring the expression of down-stream genes. In some embodiments, gene expression monitoring is used to determine function of an allele of a BRCA1 gene by monitoring expression of its down-stream regulated genes. Similar embodiments use gene expression to discern the effect of specific mutations of BRCA1 genes. Gene expression is also used to identify potential anti-neoplastic agents in some embodiments.

BRIEF DESCRIPTION OF THE DRAWINGS

The file of this patent contains at least one drawing executed in color. Copies of this patent with color drawing (s) will be provided by the Patent and Trademark Office upon request and payment of te necessary fee.

FIG. 1: Inducible expression of BRCA1.

FIG. 2: Induction of cell death by BRCA1: p53-independence and inhibition by bcl2.

FIG. 3: Activation of JNK/SAPK by BRCA1

FIG. 6: Identification of candidate BRCA1 targets by hybridization to oligonucleotide arrays (FIG. 6A) Summary of results from hybridization to oligonucleotide arrays representing 6,800 expressed sequences. Labeled RNA probes derived from UBR60-bcl2 cells grown in the presence of tetracycline, or 6, 12 and 24 hrs following withdrawal of tetracycline were hybridized to the arrays. Fold induction by northern analysis (at 24 hrs) is determined by phosphorimager quantitation. All genes showing at least 2-fold induction by northern blotting are listed.

FIG. 7: Induction of GADD45 by BRCA1

DETAILED DESCRIPTION OF THE INVENTION

Figure 1A:
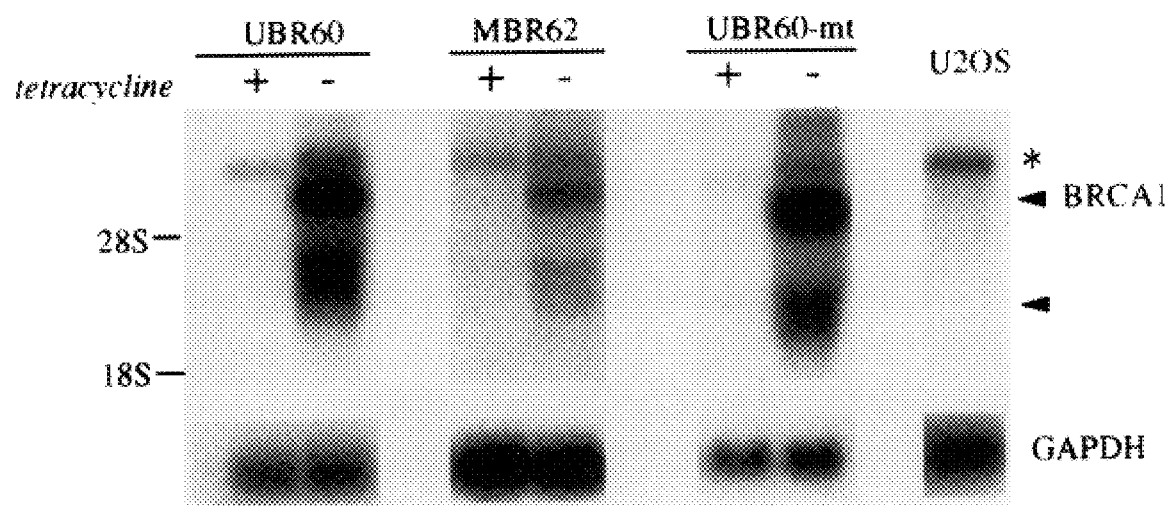
(FIG. 1A) Northern blot analysis of total cellular RNA from U2OS cells and derived lines with inducible expression of BRCA1, UBR60 and UBR60mt (mutant), and from the MDA435-derived cells MBR62, grown in the presence of tetracycline and 24 hrs after tetracycline withdrawal, and probed with BRCA1 cDNA (nucleotides 2,436 to 4,058). The endogenous transcript is denoted by an asterisk; inducible full length BRCA1 is labeled by an arrowhead, along with smaller mRNA species, most of which are not polyadenylated. Blots were reprobed with GAPDH (loading control)

To address the functional properties of BRCA1 and examine its effect on endogenous target genes, we developed cells in which a tightly regulated inducible promoter allowed expression of the full length protein. Forced expression of BRCA1 in these cells triggered apoptosis through activation of the JNK/SAPK pathway. Cells in which JNK/SAPK signaling was disrupted demonstrated characteristics of cellular senescence following inducible expression of BRCA1. Oligonucleotide array-based expression profiling revealed a small number of genes exhibiting altered expression following BRCA1 induction. Among these candidate BRCA1 targets, the DNA damage responsive gene GADD45 showed the most dramatic induction.

Defining the functional properties of BRCA1 has been hampered by the early lethality of BRCA1-null mice and by the absence of cell lines completely lacking BRCA1 expression (Hakem et al., 1996; Liu et al., 1996). In fact, the overexpression of p53 and p21 in BRCA1-null embryos has been interpreted as evidence that homozygous loss of BRCA1 may not be tolerated by cells in the absence of additional genetic alterations. Similarly, constitutive expression of exogenous BRCA1 has proved difficult, and experiments to date have involved truncated constructs (Shao et al., 1996; Holt et al., 1996). The use of tightly regulated inducible expression thus allows analysis of cells expressing full length wild-type BRCA1. The consequences of BRCA1 overexpression in U2OS and MDA435 cells can only provide a simplistic model of its physiological function, which may also be modulated by protein phosphorylation and possible interactions with other coregulated proteins (Wu et al., 1996; Ruffner and Verma, 1997; Scully et al., 1997c; Thomas et al., 1997). However, regulated overexpression of tumor suppressors, such as p53, has proven particularly useful for identifying critical downstream target genes and potential functional pathways (El-Deiry et al., 1993; Hermeking et al., 1997; Polyak et al., 1998). The magnitude of inducible expression observed in these cells (approximately 60-fold BRCA1 mRNA induction and 10-fold protein induction) is consistent with the elevated expression levels observed in tissues undergoing proliferation and differentiation (Lane et al., 1995; Marquis et al., 1995).

In contrast to GADD45, we have not observed altered expression of other p53 target genes, including p21, following inducible expression of BRCA1. As noted above, conflicting observations have suggested that BRCA1 may directly induce the p21 promoter (Somasundaram et al., 1997) or cooperate with p53 in inducing this promoter (Ouichi et al., 1998), whereas increased expression of p21 was demonstrated by analysis of BRCA1-null embryos, suggesting an antagonistic relationship between BRCA1 and p53 (Hakem et al., 1997; Ludwig et al., 1997). Our observations suggest that the effect of BRCA1 on the p21 promoter is not associated with a physiological effect on the endogenous gene, at least in the cell lines that we examined. Appreciation of the role of BRCA1 in the response to DNA damage suggests that the activation of p53 and increased expression of p21 in BRCA1-null embryos is likely to be an indirect result from the accumulation of DNA damage in these cells. A similar interpretation has been proposed for the activation of p53 in cells lacking other signaling pathways such as ATM (Westphal et al., 1997a and b).

The identification of downstream targets of BRCA1 by expression profiling using oligonucleotide arrays demonstrates the potential utility of this strategy in defining functional pathways for individual gene products (Lockhart et al., 1996; Wodicka et al., 1997). Forced expression of BRCA1 may not by itself recapitulate its physiological activation, although the signal amplification associated with this system facilitates the detection of target genes. Target genes for p53 and APC have also been identified using an overexpression model and SAGE, a strategy that requires sequencing large numbers of multimerized cDNA tags (Velculescu et al., 1995; Hermeking et al., 1997; Polyak et al., 1998; He et al., 1998). By comparison, hybridization-based expression profiling affords high-throughput analysis of multiple specimens. Expression profile analyses in yeast have been reported using oligonucleotide arrays, allowing the demonstration of altered gene expression patterns associated with different growth conditions, genetic backgrounds, and cell cycle inhibitors (Wodicka et al., 1997; Cho et al., 1998; Gray et al., 1998). Similar comparisons in mammalian cells have been predicted to show large differences in expression patterns between different tissues, and between normal and cancer cells (Southern, 1996). Our observations now demonstrate the application of this approach to defining specific downstream targets for an individual gene product. This analysis requires the ability to reliably detect expression changes in a smaller number of genes and of lower magnitude than for comparison between grossly different cell types. Our experiments indicate that many potential BRCA1 targets registered by oligonucleotide arrays were confirmed by Nothern blotting, supporting the accuracy of this technique. In most cases, discrepancies were attributable to the lower sensitivity of northern analysis, although in some cases, inter-replicate variation may have contributed to discordant results. Monitoring the time course of target gene induction following BRCA1 expression, and analyzing results derived from multiple experimental replicates, appear to be ta valuable strategy for the identification of specific downstream targets. As more complex comparisons of expression profiles are undertaken, and as array density is increased to cover all known transcription units in mammalian cells, the optimization of experimental approaches and the development of novel data mining tools will become invaluable.

Expression of a gene can be detected and monitored using any available and convenient technique known in the art. Any expression product can be monitored, including but not limited to mRNA and protein. Techniques for monitoring and detecting mRNA transcripts include, but are not limited to RTPCR, Northern blotting, hybridization in solution, hybridization on a solid support, hybridization on an array. Techniques for monitoring and detecting protein include immunoblotting, enzyme assays, immunohistochemistry.

The methods of the present invention can employ detection of expression of one or more downstream genes of BRCA1. These may be up- or down-regulated genes. A plurality of such genes may be monitored or a single of the genes may provide sufficiently reliable information. The results of a plurality of genes can be statistically treated and/or combined to arrive at an accurate assessment of the status of BRCA1. Particular genes which are downstream of BRCA1 are identified in FIG. 6A. Others can also be used in combination with those disclosed here. A change in expression of one or more downstream genes from the wild-type BRCA1 pattern indicates a functional alteration in BRCA1, such as a mutation which affects BRCA1 transcriptional activation. Some mutations in BRCA1 may not affect function at all. Other mutations may not affect BRCA1's transcription regulatory role.

Changes in the expression of downstream gene need not be dramatic in magnitude. Even small changes, such as ±50%, can be sufficient if the change is reproducibly associated with a change in BRCA1 status. However, changes of larger magnitude may be easier to detect using techniques which are less sensitive. Thus a cut-off can be set at a change of two-fold, three-fold, four-fold, five-fold, ten-fold, twenty-fold, thirty-fold, and fifty-fold. As the cut-off threshold is raised, fewer downstream genes will be informative.

Reference or control samples, according to the invention are those which are known to have wild-type BRCA1, those known to be non-neoplastic, or those which have not been contacted with a test compound. Appropriate reference or control samples can be readily selected by those of skill in the art, depending on the purpose of the comparison to be made. When testing the affect of a mutation in BRCA1, a reference sample will be substantially similar to the sample with the mutation, but for the mutation in BRCA1. Thus the two samples being compared will preferably be as similar to each other as possible. In the case of cell lines being tested, isogeneic cell lines are preferred. In the case of biopsy samples, test and reference samples from the same individual are preferred, with samples from the same organ of the same individual more preferred.

Computers can be used to detect expression as well as to store, process, and compare data. Data can be input manually or automatically, for example by storing of optical data which represents an output of an expression monitoring assay. Two sets of input data can be compared to determine whether statistically significant changes in expression have occurred. Threshold levels for determining significant changes can be set, as described above, at different levels. The lower the threshold change is set, the more data points will be potentially obtainable for different genes' expression.

Since BRCA1 mutations have been found to be correlated with familial breast and ovarian cancer, detection of the results of such mutations, i.e., in the expression of downstream genes, may be a useful way to score a BRCA1-null genotype. The null genotype correlates with neoplasia, rather than predisposition. Because BRCA1 is such a large gene, an expression test of downstream genes may represent a more convenient and economical way to score mutations than traditional mutation screening techniques. In addition, the presence of the null genotype may provide additional prognostic information as well as information regarding particular drug sensitivities and resistances.

Expression monitoring of BRCA1-downstream genes provides an attractive means for high through-put drug screening. The effect of a drug on a living cell can be assessed. Drugs which provide the same transcriptional regulatory effect as BRCA1 itself are attractive candidates, inter alia, for treating breast and ovarian cancers involving BRCA1 mutations. Any mammalian cell can be used in such a screen, although preferably a human cell will be used. More preferably the cell will be a tumor cell. More preferred is that the tumor cell will be a breast or ovarian cancer cell.

1. Definitions

Bind(s) substantially: "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

Background: The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is mammalian nucleic acids). Background can also be calculated as the average signal intensity produced by regions of the array that lack any probes at all.

Hybridizing specifically to: The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) DNA or RNA.

Mismatch control: The term "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases. While the mismatch(s) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

mRNA or transcript: The term "mRNA" refers to transcripts of a gene. Transcripts are RNA including, for example, mature messenger RNA ready for translation, products of various stages of transcript processing. Transcript processing may include splicing, editing and degradation.

Nucleic Acid: The terms "nucleic acid" or "nucleic acid molecule" refer to a deoxyribonucleotide or ribonucleotide polymer in either single-or double-stranded form, and unless otherwise limited, would encompass analogs of natural nucleotide that can function in a similar manner as naturally occurring nucleotide. A n oligo-nucleotide is a single-stranded nucleic acid of 2 to n bases, where n may be greater than 500 to 1000. Nucleic acids may be cloned or synthesized using any technique known in the art. They may also include non-naturally occurring nucleotide analogs, such as those which are modified to improve hybridization and peptide nucleic acids.

Nucleic acid encoding a regulatory molecule: The regulatory molecule may be DNA, RNA or protein. Thus for example DNA sites which bind protein or other nucleic acid molecules are included within the class of regulatory molecules encoded by a nucleic acid.

Perfect match probe: The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe"

Probe: As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

Target nucleic acid: The term "target nucleic acid" refers to a nucleic acid (often derived from a biological sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

Stringent conditions: The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Subsequence: "Subsequence" refers to a sequence of nucleic acids that comprise a part of a longer sequence of nucleic acids.

Thermal melting point (Tm): The Tm is the temperature, under defined ionic strength, pH, and nucleic acid concentration, at which 50% of the probes complementary to the target sequence hybridize to the target sequence at equilibrium. As the target sequences are generally present in excess, at Tm, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotide). Stringent conditions may also be achieved with the addition of destabilizing agents such as formamide.

Quantifying: The term "quantifying" when used in the context of quantifying transcription levels of a gene can refer to absolute or to relative quantification. Absolute quantification may be accomplished by inclusion of known concentration(s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Sequence identity: The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Methods of alignment of sequences for comparison are well known in the art. Optimal alignment of sequences for comparison may be conducted by the local homology algorithm of Smith and Waterman, *Adv. Appl. Math.* 2: 482 (1981), by the homology alignment algorithm of Needleman and Wunsch *J. Mol. Biol.* 48: 443 (1970), by the search for similarity method of Pearson and Lipman, *Proc. Natl. Acad. Sci. USA* 85: 2444 (1988), by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA), or by inspection. In particular, methods for aligning sequences using the CLUSTAL program are well described by Higgins and Sharp in *Gene,* 73: 237–244 (1988) and in *CABIOS* 5: 151–153 (1989)).

Up-stream or down-stream gene. If the expression of a first gene is regulated by a second gene, the second gene is called an "up-stream gene" for the first gene and the first gene is the "down-stream" gene of the second gene. The regulation of the first gene by second gene could be through trans-activation. For example, the first gene encodes a transcriptional factor that controls the expression of the second gene. The regulation can also be exerted by cis-acting. For example, the first gene is in the proximity of the second gene and exerts a positional effect on the expression of the second gene. In this case, the first gene does not have to be expressed in order to have an influence on the second gene.

Activity of a gene is reflected by the activity of its product(s): the proteins or other molecules encoded by the gene. Those product molecules perform biological functions. Directly measuring the activity of a gene product is, however, often difficult for certain genes. Instead, the immunological activities or the amount of the final product(s) or its peptide processing intermediates are determined as a measurement of the gene activity. More frequently, the amount or activity of intermediates, such as transcripts, RNA processing intermediates, or mature mRNAs are detected as a measurement of gene activity.

In many cases, the form and function of the final product (s) of a gene is unknown. In those cases, the activity of a gene is measured conveniently by the amount or activity of transcript(s), RNA processing intermediate(s), mature mRNA(s) or its protein product(s) or functional activity of its protein product(s).

Any methods that measure the activity of a gene are useful for at least some embodiments of this invention. For example, traditional Northern blotting and hybridization, nuclease protection, RT-PCR and differential display have been used for detecting gene activity. Those methods are useful for some embodiments of the invention. However, this invention is most useful in conjunction with methods for detecting the expression of a large number of genes.

High density arrays are particularly useful for monitoring the expression control at the transcriptional, RNA processing and degradation level. The fabrication and application of high density arrays in gene expression monitoring have been disclosed previously in, for example, WO 97/10365, WO 92/10588, U.S. application Ser. No. 08/772,376 filed Dec. 23, 1996; Ser. No. 08/529,115 filed on Sep. 15, 1995; Ser. No. 08/168,904 filed Dec. 15, 1993; Ser. No. 07/624,114 filed on Dec. 6, 1990, Ser. No. 07/362,901 filed Jun. 7, 1990, all incorporated herein for all purposed by reference. In some embodiment using high density arrays, high density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high density array of oligonucleotides and then the amount of target nucleic acids hybridized to each probe in the array is quantified. One preferred quantifying method is to use confocal microscope and fluorescent labels. The GeneChip® system (Affymetrix, Santa Clara, Calif.) is particularly suitable for quantifying the hybridization; however, it will be apparent to those of skill in the art that any similar systems or other effectively equivalent detection methods can also be used.

High density arrays are suitable for quantifying a small variations in expression levels of a gene in the presence of a large population of heterogeneous nucleic acids. Such high density arrays can be fabricated either by de novo synthesis on a substrate or by spotting or transporting nucleic acid sequences onto specific locations of substrate. Nucleic acids are purified and/or isolated from biological materials, such as a bacterial plasmid containing a cloned segment of sequence of interest. Suitable nucleic acids are also produced by amplification of templates. As a nonlimiting illustration, polymerase chain reaction, and/or in vitro transcription, are suitable nucleic acid amplification methods.

Synthesized oligonucleotide arrays are particularly preferred for this invention. Oligonucleotide arrays have numerous advantages, as opposed to other methods, such as efficiency of production, reduced intra- and inter array variability, increased information content and high signal-to-noise ratio.

Preferred high density arrays for gene function identification and genetic network mapping comprise greater than about 100, preferably greater than about 1000, more preferably greater than about 16,000 and most preferably greater than 65,000 or 250,000 or even greater than about 1,000,000 different oligonucleotide probes, preferably in less than 1 $cm^2$ of surface area. The oligonucleotide probes range from about 5 to about 50 or about 500 nucleotides, more preferably from about 10 to about 40 nucleotide and most preferably from about 15 to about 40 nucleotides in length.

Massive Parallel Gene Expression Monitoring

One preferred method for massive parallel gene expression monitoring is based upon high density nucleic acid arrays. Nucleic acid array methods for monitoring gene expression are disclosed and discussed in detail in PCT Application WO 092.10588 (published on Jun. 25, 1992), all incorporated herein by reference for all purposes.

Generally those methods of monitoring gene expression involve (a) providing a pool of target nucleic acids comprising RNA transcript(s) of one or more target gene(s), or nucleic acids derived from the RNA transcript(s); (b) hybridizing the nucleic acid sample to a high density array of probes and (c) detecting the hybridized nucleic acids and calculating a relative and/or absolute expression (transcription, RNA processing or degradation) level.

(A) Providing a Nucleic Acid Sample

One of skill in the art will appreciate that it is desirable to have nucleic samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Transcripts, as used herein, may include, but not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, such sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (dT) column contains RNA molecules with poly (A) tails. Those polyA$^+$ RNA molecules could be mature mRNA, RNA processing intermediates, nascent transcripts or degradation intermediates.

Biological samples may be of any biological tissue or fluid or cells from any organism. Frequently the sample will be a "clinical sample" which is a sample derived from a patient. Clinical samples provide a rich source of information regarding the various states of genetic network or gene expression. Some embodiments of the invention are employed to detect mutations and to identify the phenotype of mutations. Such embodiments have extensive applications in clinical diagnostics and clinical studies. Typical clinical samples include, but are not Limited to, sputum, blood, blood cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network. One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase is inhibited or destroyed by heat treatment followed by proteinase treatment.

Methods of isolating total mRNA are also well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993)).

In a preferred embodiment, the total RNA is isolated from a given sample using, for example, an acid guanidinium-phenol-chloroform extraction method and polyA$^+$ mRNA is isolated by oligo(dT) column chromatography or by using (dT) on magnetic beads (see, e.g., Sambrook et al., *Molecular Cloning. A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 ERNA is combined with RNA isolated from the sample according to standard techniques known to those of skilled in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in PCR Protocols, *A Guide to Methods and Applications*, Innis et al., Academic Press, Inc. N.Y., (1990).

Other suitable amplification methods include, but are not limited to polymerase chain reaction (PCR) (Innis, et al., PCR Protocols. *A guide to Methods and Application*. Academic Press, Inc. San Diego, (1990)), ligase chain reaction (LCR) (see Wu and Wallace, *Genomics*, 4: 560 (1989), Landegren, et al., *Science*, 241: 1077 (1988) and Barringer, et al., *Gene*, 89: 117 (1990), transcription amplification (Kwoh, et al., *Proc. Natl. Acad. Sci. USA*, 86: 1173 (1989)), and self-sustained sequence replication (Guatelli, et al, *Proc. Nat. Acad. Sci. USA*, 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. A one-tube mRNA capture method may be used to prepare poly(A)$^+$ RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo(dT) and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, (supra) and this particular method is described in detail by Van Gelder, et al., *Proc. Natl. Acad. Sci. USA*, 87: 1663–1667 (1990) who demonstrate that in vitro amplification according to this method preserves the relative frequencies of the various RNA transcripts. Moreover, Eberwine et al. *Proc. Natl. Acad. Sci. USA*, 89: 3010–3014 provide a protocol that uses two rounds of amplification via in vitro transcription to achieve greater than 106 fold amplification of the original starting material, thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluescript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., *Gene*, 88: 25–36 (1990)).

(B) Hybridizing nucleic acids to high density arrays

1. Probe design

One of skill in the art will appreciate that an enormous number of array designs are suitable for the practice of this invention. The high density array will typically include a number of probes that specifically hybridize to the sequences of interest. In addition, in a preferred embodiment, the array will include one or more control probes.

The high density array chip includes "test probes." Test probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiments, test probes are double or single strand DNA sequences. DNA sequences are isolated or cloned from nature sources or amplified from nature sources using nature nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as 1) normalization controls; 2) expression level controls; and 3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary subsequences of constitutively expressed "housekeeping genes" including, but not limited to the β-actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases.

A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (I(PM)-I(MM)) provides a good measure of the concentration of the hybridized material. The high density array may also include sample preparation/amplification control probes. These are probes that are complementary to subsequences of control genes selected because they do not normally occur in the nucleic acids of the particular biological sample are assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 2-mer sequence complementary to an IL-2 mRNA.

However, there may exist 20-mer subsequences that are not unique to the IL-2 mRNA. Probes directed to these subsequences are expected to cross-hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

In addition, in a preferred embodiment, expression monitoring arrays are used to identify the presence and expression (transcription) level of genes which are several hundred base pairs long. For most applications it would be useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

As disclosed in U.S. application Ser. No. 08/772,376, probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

2. Forming High Density Arrays

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523 which disclose methods of forming vast arrays of peptides, oligonucleotides and other molecules using, for example, light-directed synthesis techniques. See also, Fodor et al., *Science,* 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854. Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in copending applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate. After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthesized or natural nucleic acids in predetermined positions. Synthesized or natural nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

3. Hybridization

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6× SSPE-T at 37° C. (0.005% Triton X-100) to ensure hybridization and then subsequent washes are performed at higher stringency (e.g., 1× SSPE-T at 37° C.) to eliminate mismatched hybrid duplexes. Successive washes may be performed at increasingly higher stringency (e.g., down to as low as 0.25× SSPE-T at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g, C-TAB) or a blocking reagent (e.g., sperm DNA, cot-1 DNA, etc.) during the hybridization to reduce non-specific binding. In a particularly preferred (embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.) The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology*, Vol. 24: *Hybridization With Nucleic Acid Probes*, P. Tijssen, ed. Elsevier, N.Y., (1993)).

(C) Signal Detection

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. One particular preferred methods uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology*, Vol. 24: *Hybridization With Nucleic Acid Probes*, P. Tijssen, ed. Elsevier, N.Y., (1993)). Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high density array are known to those of skill in the art. Thus, for example, where a colorimetric label is used, simple visualization of the label is sufficient. Where a radioactive labeled probe is used, detection of the radiation (e.g. with photographic film or a solid state detector) is sufficient. In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No: 5,143,854, PCT Application 20 92/10092, and copending U.S. application Ser. No. 08/195,889 filed on Feb. 10, 1994. Use of laser illumination in conjunction with automated confocal microscopy for signal detection permits detection at a resolution of better than about 100 $\mu$m, more preferably better than about 50 $\mu$m, and most preferably better than about 25 $\mu$m. One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal. In addition, the provision of appropriate controls permits a more detailed analysis that controls for variations in hybridization conditions, cell health, non-specific binding and the like. Thus, for example, in a preferred embodiment, the hybridization array is provided with normalization controls. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplification control probes (e.g., the Bio B probes). The resulting values may be multiplied by a constant value to scale the results.

As indicated above, the high density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control both show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

In some preferred embodiments, a computer system is used to compare the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes.

After the system compares the hybridization intensity of the perfect match and mismatch probes, the system indicates expression of the gene. As an example, the system may indicate to a user that the gene is either present (expressed), marginal or absent (unexpressed). Specific procedures for data analysis is disclosed in U.S. application Ser. No. 08/772,376, previously incorporated for all purposes.

In addition to high density nucleic acid arrays, other methods are also useful for massive gene expression monitoring. Differential display, described by Liang, P. and Pardee, A. B. (Differential Display of eukaryotic messenger RNA by means of the polymerase chain reaction. *Science* 257:967–971, 1992, incorporated herein by reference for all purposes) provides a useful mean for distinguishing gene expression between two samples. Serial analysis of gene expression, described by Velculescu et al. (Serial Analysis of Gene Expression. Science, 270:484–487, 1995, incorporated herein by reference for all purposes) provides another method for quantitative and qualitative analysis of gene expression Optical fiber oligonucleotide sensors, described by Ferguson et al. (A Fiber-optic DNA biosensor microarray for the analysis of gene expression. Nature-Biotechnology 14:1681–1684, 1996), can also be used for gene expression monitoring.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes

EXAMPLES

Example 1

Inducible expression of BRCA1

Figure 1B:
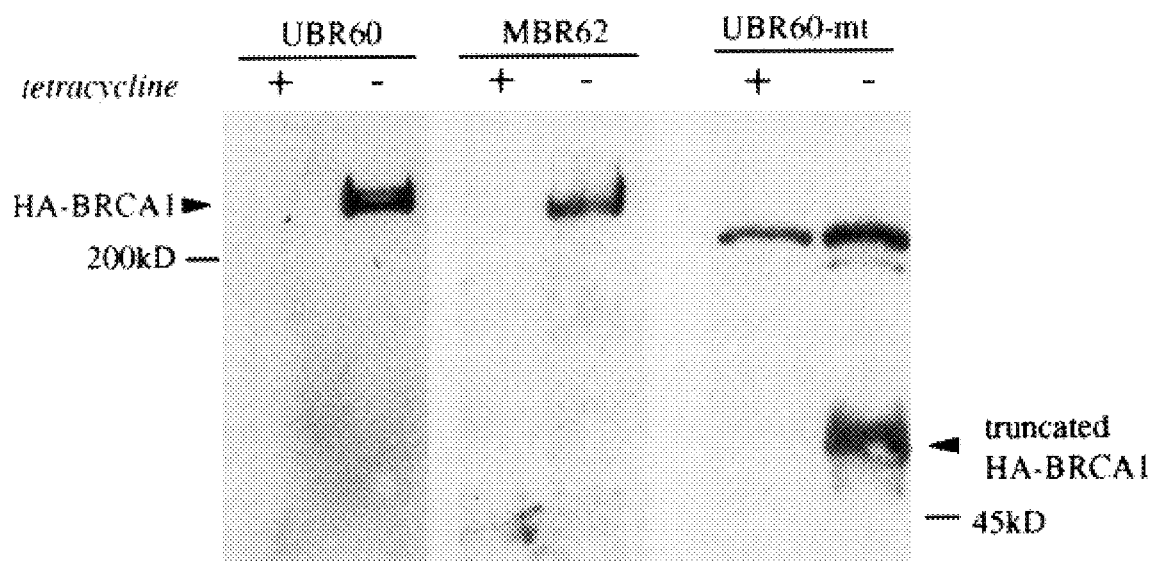
(FIG. 1B) Immunoblotting analysis of BRCA1 immunoprecipitates, showing tightly regulated inducible expression of the full length protein in UBR60 and MBR62 cells and of the truncated mutant in UBR60mt cells. The 12-CA-5 antibody, directed against the synthetic HA N-terminal epitope, was used to probe cellular lysates immunoprecipitated using either the C-terminal antibody C20 (for full length BRCA1) or the N-terminal antibody D20 (for the truncated product). The C20 antibody is known to also recognize an epitope within the epidermal growth factor receptor, but this cross-reactivity is no longer of concern when combined with immunoblotting using antibody to the HA-epitope.

To study the functional properties of BRCA1, we established inducible, tetracyline-regulated expression (Gossen and Bujard, 1992) in two cell types: U13R60 cells, derived from the U2OS osteosarcoma cell line and MBR62 cells, derived from the MDA435 breast cancer cell line. Northern and Western blot analyses in both cell lines showed tightly regulated induction of BRCA1 expression (FIG. 1A, B). Low levels of endogenous 7.8 kb BRCA1 mRNA were detectable when cells were grown in the presence of tetracycline, and drug withdrawal led to induction of the expected 5.6 kb transfected BRCA1 transcript. A number of smaller mRNA species were also observed, presumably resulting from the activation of cryptic splice sites within the transfected cDNA (Thakur et al., 1997; Wilson et al., 1997; see Experimental Procedures), but these comprised only a small fraction of the polyadenylated transcript (data not shown). Analysis of inducible protein expression, using immunoprecipitation with antibody C20 directed against the C-terminus of BRCA1, followed by immunoblotting using antibody 12-CA-5 against the N-terminal epitope tag, identified only the expected 220 kD full length BRCA1 (FIG. 1B). U2OS cells were also generated with inducible expression of a mutant BRCA1 allele, containing a stop codon in the central exon 11, a common site of breast cancer-associated truncating mutations (UBR60-mt cells). These cells also demonstrated tightly regulated expression of the mutant transcript and of the expected truncated protein of 50 kD, identified by immunoprecipitation with the N-terminal antibody D-20, followed by Western analysis with 12-CA-5 (FIGS. 1A and 1B).

Figure 1C:
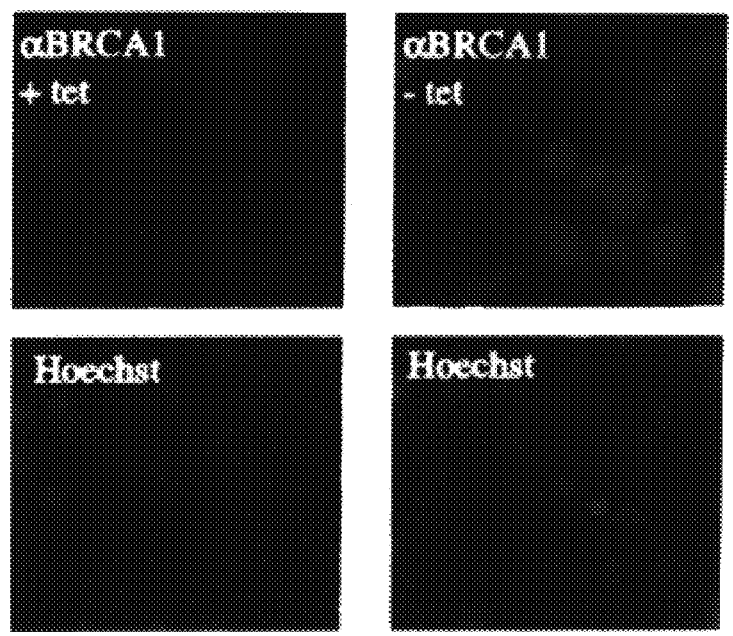
(FIG. 1C) Immunofluorescence analysis of UBR60 cells grown in the presence or absence of tetracycline. Antibody MS 13 recognizes both endogenous and inducible BRCA1, making it possible to demonstrate cellular heterogeneity in expression levels of the inducible construct. Hoechst staining is shown to demonstrate primarily nuclear staining of BRCA1.
Figure 1D:
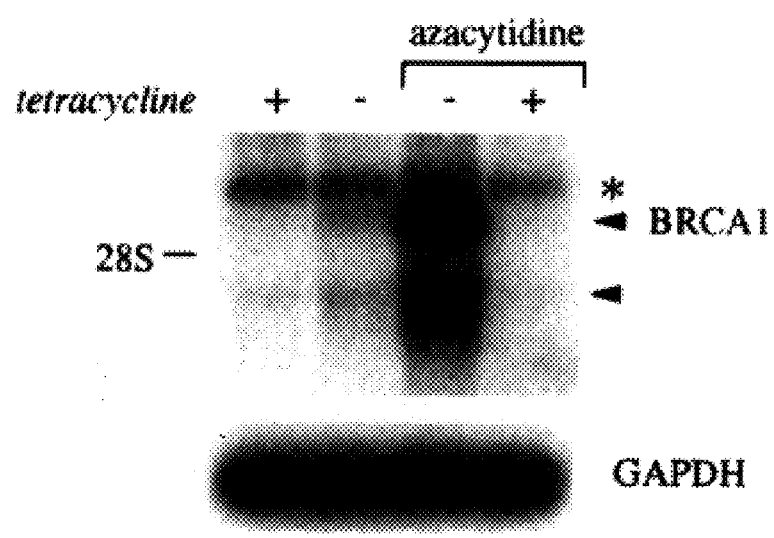
(FIG. 1D) Northern blot analysis showing restoration of BRCA1 expression by 5-azacytidine treatment of cells that had lost inducible expression following prolonged growth in the presence of tetracycline. Presumptive methylation of the inducible promoter directing BRCA1 expression contributes to cellular heterogeneity of inducible expression in UBR60 cells.

We used immunofluorescence analysis, with antibody MS13 directed against the N-terminus of BRCA1 (Scully et al., 1996), to compare expression of inducible BRCA1 with that of the endogenous protein within individual cells (FIG. 1C). Nuclear expression of inducible BRCA1 was evident, although some cytoplasmic staining was also observed in a few cells expressing very high levels of BRCA1. Similar results were obtained with antibody 12-CA-5 (data not shown). Cellular heterogeneity, a common feature of tetracyline-inducible cell lines, was evident following withdrawal of tetracycline, with the range of inducible expression estimated as 2-10 fold that of the endogenous protein. This relatively modest protein induction, compared with the more dramatic induction of BRCA1 mRNA (FIG. 1A) is consistent with reduced translational efficiency of the transfected transcript. It was of interest to note that UBR60 cells lost inducible BRCA1 expression following continued growth in tetracycline, despite retaining the ability to express a transiently transfected tetracycline-responsive reporter (data not shown). Treatment with 5-azacytidine promptly restored inducible BRCA1 expression in these cells (FIG. 1D), suggesting that hypermethylation of the tetracycline-responsive BRCA1 promoter was responsible for its suppression (Cedar, 1988), and presumably for the heterogeneity of BRCA1 expression in these cells.

Experimental Procedures:

Generation of cells with inducible BRCA1 expression

A full length BRCA1 construct was assembled from partial cDNA clones isolated from a human testis cell library, confirmed as wild-type by sequencing the entire coding region, and cloned, along with a 5' HA epitope tag, downstream of the tetracycline-regulated promoter in pUHD10-3 (Gossen and Bujard 1992). A mutant BRCA1 construct was generated by PCR, causing premature termination within exon 11 (nucleotide 1,259) and encoding a truncated protein of 50 kD. An U2OS osteosarcoma founder cell line UAT5 stably expressing the tetracycline-VP16 transactivator (200-fold induction of a transiently transfected reporter construct) was used to generate stably transfected clones: UBR60, with tightly regulated inducible expression of wild-type BRCA1, and UBR-mt with comparable expression the mutant construct. The breast cancer cell line MDA435 was used to generate another founder cell line, MIDA47, with 200-fold induction of a transiently transfected reporter construct, from which was derived the MBR62 cell line with inducible wild-type BRCA1. Total cellular RNA was isolated using RNA Stat60 reagent (Teltest Inc.), and electrophoresed in 1% agarose/formaldehyde gels, followed by transfer to Hybond N (Amersham) and northern blotting. Endogenous BRCA1 was expressed at low levels in both cell lines, with minimal expression of the native BRCA1-D11 alternative splice variant lacking the large central exon 11 (Thakur et al., 1997; Wilson et al., 1997). In addition to the full length inducible BRCA1 transcript, smaller inducible mRNAs were evident, which were mapped using cDNA probes interspersed along the coding region and examined for correct processing by analysis of poly A-selected RNA. A polyadenylated transcript of 3 kb was identified by both 5' and 3' probes, while a non-polyadenylated transcript of 4 kb was recognized by a probe spanning exon 11. These transcripts presumably resulted from the activation of cryptic splice sites within the cDNA sequence, but they did not encode proteins detectable using either C or N-terminal antibodies.

To test for promoter hypermethylation, UBR60 cells that had lost inducible expression following prolonged growth in tetracycline were treated with 2 mg/ml 5-azaC (Sigma) for 24 hrs on days 1 and 4 (Shin et al., 1992), followed by withdrawal of tetracycline on day 7, RNA isolation on day 8 and Northern blot analysis. Cell lines with constitutive expression of CMV-driven bcl2 or HPV16E6 were generated by stable transfection of UBR60 cells along with a hygromycin-resistance plasmid. Cells with constitutive expression of the CMV-driven dominant negative SEK1 mutant (kindly provided by L. Zon, Harvard Medical School) were generated by cotransfection with XGPT and selection in HAT. Multiple clones expressing the stably transfected constructs were analyzed to ensure against the effects of clonal selection. To inhibit caspases required for programmed cell death, cells were treated with the synthetic, cell permeable, non-cleavable analog of caspase CPP32 (0.2 mM; Clontech). Colony formation was assayed by withdrawal of tetracycline and staining of colonies after 7 days in culture. For growth curves, viable cells were counted using staining with methylene blue.

Antibodies and immunological analyses

Antibodies against BRCA1 included the mouse monoclonal antibody MS13 (Oncogene Science), the rabbit polyclonal antibodies C20 and D20 (Santa Cruz) and monoclonal antibody 12-CA-5 directed against the synthetic HA epitope (provided by E. Harlow, MGH). Antibody against p21 (CP36) and p53 (PAb122) were kindly provided by E. Harlow, and antibodies to bax (N20), PARP (C2-10) were purchased from Santa Cruz and Biomol respectively. Tunel assays were performed using standard protocols (Oncor). Expression of BRCA1 was demonstrated by extraction of cellular lysates using RIPA buffer, immunoprecipitation with antibodies C20 or D20 (Santa Cruz), followed by Western blot analysis using antibody 12-CA-5 to the HA epitope. Activation of JNK/SAPK was measured 24 hrs following induction of BRCA1 expression, before apoptotic cells were evident. Cellular lysates were extracted, standardized for protein content, immunoprecipitated with antibody to JNK/SAPK (C17; Santa Cruz), and incubated with GST-c-Jun in the presence of 32P-gATP. To demonstrate uv-mediated induction of JNK/SAPK activity, lysates were prepared from cells grown in the presence of tetracycline, 1 hr after treatment of cells with 20J/m2 of uv-B, the peak of JNK/SAPK activation by uv-irradiation. As a control, apoptosis was triggered in U2OS cells with stable expression of a temperature-sensitive p53 (tsp53) by growth at 32° C. for 24 hrs. Activation of the MAP kinase pathway was analyzed by immunoblotting of cellular lysates using antibody against p42 and p44 MAP kinase (Erk1 and Erk2) and the catalytically activated, Tyr204 phosphorylated forms (p14/p42 MAPK and phospho-MAPK antibodies; New England Biolabs).

For immunofluorescence analysis, cells were grown on coverslips, fixed with 4% paraformaldehyde, permeabilized with 1% Nonidet P-40/10 mM glycine, preadsorbed with 3% bovine serum albumin, treated with antibody M5S13 (1:200) or 12-CA5 (1:10) followed by rhodamine-conjugated affinity purified goat anti-mouse IgG (1:400; Jackson ImmunoResearch). Staining of cells for b-galactosidase activity was performed in cells fixed with 0.05% glutaraldehyde, using 1 mg/ml Xgal in 150 mM NaCl, 40 mM NaH2/Na2HPO4 pH6, 2 mM MgCl2, 5 mM K3Fe(CN) 6, 5 mM K4Fe(CN)6:3H2O. For flow cytometric analysis, cells were fixed in 80% ethanol, and treated with propidium iodide and RNase A, followed by analysis on a Becton Dickinson FACScan flow cytometer. At least 20,000 cells were analyzed for each sample.

Example 2
Induction of apoptosis by BRCA1

Figure 2A:
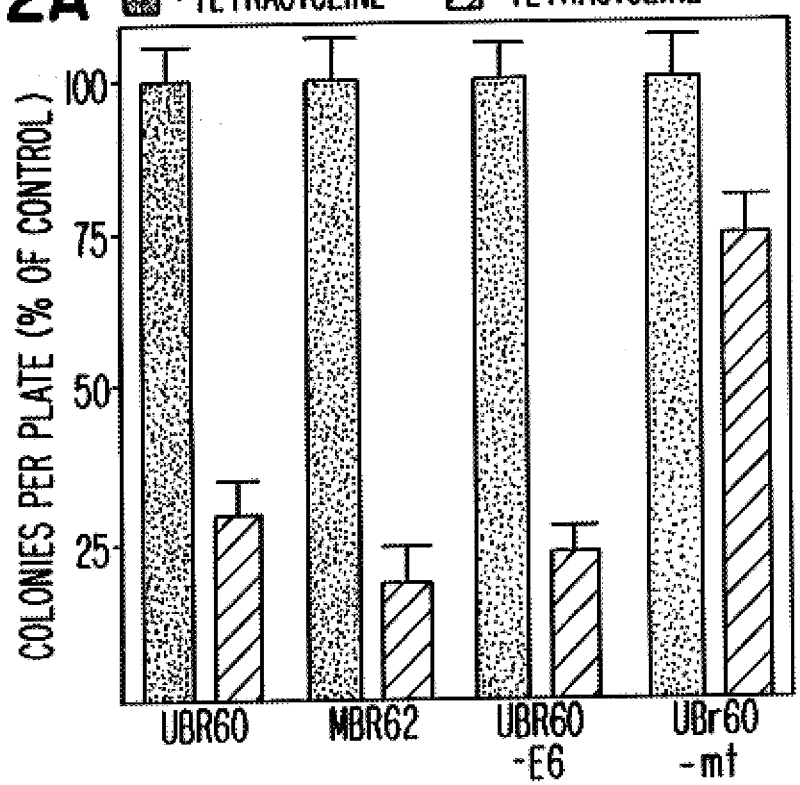
(FIG. 2A) Inhibition of colony formation by wild-type BRCA1. Colony formation by UBR60 cells (wild-type p53), UBR60-E6 (UBR60 cells expressing stably transfected HPV E6; see FIG. 2D), and MBR62 (mutant p53), following growth in the presence or absence of tetracycline. As a control, UBR60-mt cells are shown, expressing inducible BRCA1 encoding a stop codon in exon 11. Plates were stained after 14 days in culture, and colony numbers are expressed as percent of controls. Standard deviations are given.
Figure 2C:
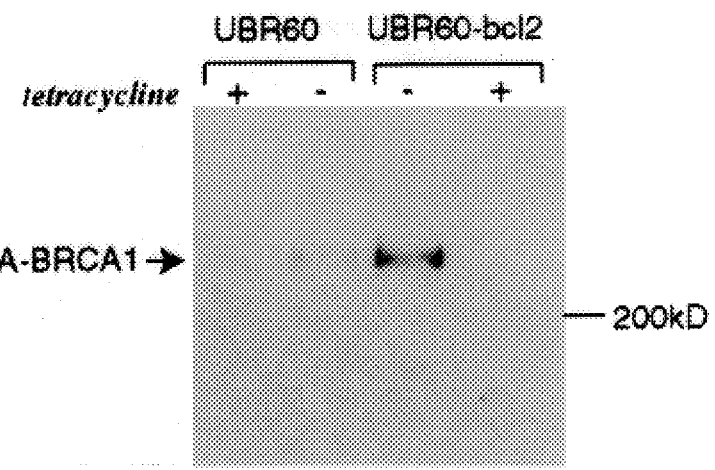
(FIG. 2C) Persistence of inducible BRCA1 protein expression in UBR60-bcl2 compared with parental UBR60 cells. Equal amounts of cellular lysates from these two cell lines, grown in the presence or absence (24 hrs) of tetracycline, immunoprecipitated with antibody C20 and analyzed by Western blot using antibody 12-CA-5, directed against the HA epitope.
Figure 2D:
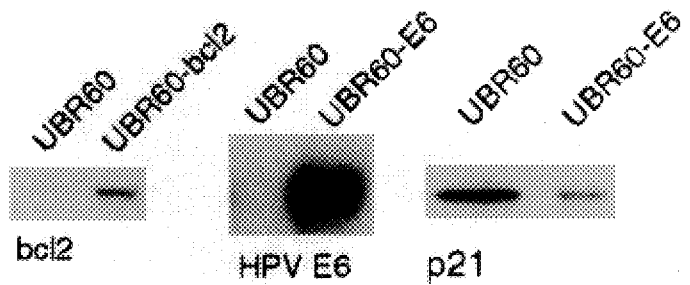
(FIG. 2D) Immunoblot of UBR60-bcl2 cells to demonstrate expression of the stably transfected CMV-driven bcl2. Northern blot of UBR60-E6 cells showing expression of the stably transfected HPV16E6, and p21-immunoblot of UBR60-E6 cells to demonstrate the reduction in p21 expression, following disruption of the endogenous p53 pathway.

To determine the effect of BRCA1 induction in UBR60 cells, we first measured their ability to form colonies in the presence or absence of tetracycline. A 4-fold reduction in colony formation was observed following induction of BRCA1 (FIG. 2A). In contrast, withdrawal of tetracycline had only a very modest effect on colony formation in UBR60-mt cells, expressing the mutant BRCA1 transcript. The inhibition of colony formation by BRCA1 was also evident in the MBR62 breast cancer cells. Of note, these cells have mutant endogenous p53 (G to E at codon 226), in contrast to U2OS cells, in which p53 is wild-type (Kastan et al., 1992). To confirm that p53, a tumor suppressor known to trigger apoptosis in response to inappropriate or conflicting growth signals, was not required for the inhibition of colony formation by BRCA1, we stably transfected UBR60 cells with human papillomavirus (HPV16) E6, which targets p53 for degradation (the resulting cells were called UBR60-E6). Western blotting confirmed the expression of E6 and the reduction in baseline p21 levels that indicates abrogation of p53 function (FIG. 2D). Induction of BRCA1 in UBR60-E6 cells inhibited colony formation to the same extent as in parental UBR60 cells, indicating that this effect was independent of p53 (FIG. 2A).

Figure 2B:
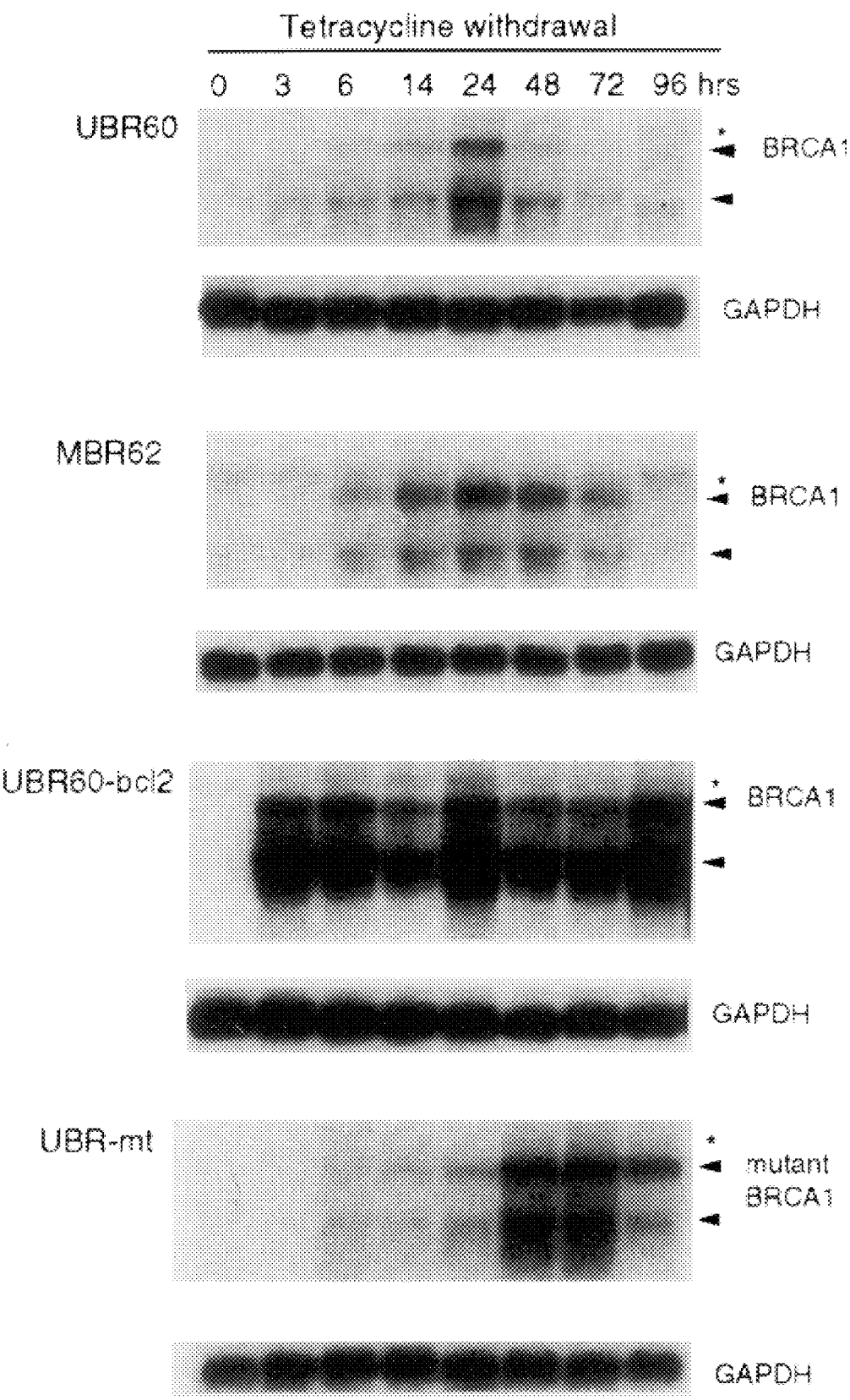
(FIG. 2B) Loss of BRCA1-expressing cells following withdrawal of tetracycline. Northern blot demonstrating the time course of BRCA1 expression following tetracycline withdrawal in UBR60, MBR62, UBR60-bcl2 (UBR60 cells expressing stably transfected bcl2 ; see FIG. 2D), and UBR60-mt cells. Due to the dramatic increase in BRCA1 expression in UBR60-bcl2 cells, a 4 hr exposure is shown, compared with a 24 hr exposure for UBR60, MBR62 and UBR60-mt cells. The endogenous BRCA1 transcript (asterisk) is shown, along with the full length inducible transcript and a shortened non-polyadenylated inducible species (arrowheads), and GAPDH (loading control).

In examining cells at early time points following withdrawal of tetracycline, we observed that expression of the induced BRCA1 transcript was unexpectedly transient. The induced BRCA1 mRNA was first detectable in both UBR60 and MBR62 cells at 6 hrs, peaked at 24 hrs and declined to virtually undetectable levels by 96 hrs (FIG. 2B). In contrast, UBR60-mt cells showed persistent expression of the mutant BRCA1 transcript. These observations raised the possibility that cells expressing wild-type BRCA1 underwent rapid cell death, leading to overgrowth by cells that had lost inducible expression through promoter hypermethylation. As expected, this effect was independent of p53, occurring both in MBR62 cells with mutant endogenous p53 (FIG. 2B) and in UBR60-E6 cells, with constitutive expression of HPV 16 E6 (data not shown). To determine whether the rapid loss of detectable BRCA1 expression resulted from apoptosis of BRCA1-expressing cells, we stably transfected these cells with a CMV-driven construct encoding the anti-apoptotic gene bcl2 (the resulting cells were called UBR60-bcl2; FIG. 2D). Constitutive expression of bcl2 prevented the loss of inducible BRCA1 expression for up to 96 hrs (FIG. 2B). To confirm that inhibition of apoptosis allowed sustained expression of BRCA1 in UBR60 cells, we also incubated these cells with caspase inhibitors, which effectively block the initiation of programmed cell death (Thornberry and Lazebnik, 1998). Consistent with the effect of bcl2, exposure of cells to synthetic, cell-permeable, non-cleavable analogs of caspase CPP32 known to inhibit apoptosis also prevented the loss of BRCA1 expression, with persistent expression for up to 96 hrs (data not shown). Continued expression of BRCA1 in UBR60-bcl2 cells eventually overwhelmed the protective effect of bcl2, resulting in cell death. However, the ability of these cells to sustain consistent expression of BRCA1 (FIG. 2C), made it possible to search for downstream targets of BRCA1.

Example 3
Activation of JNK/SAPK by BRCA1

Figure 3A:
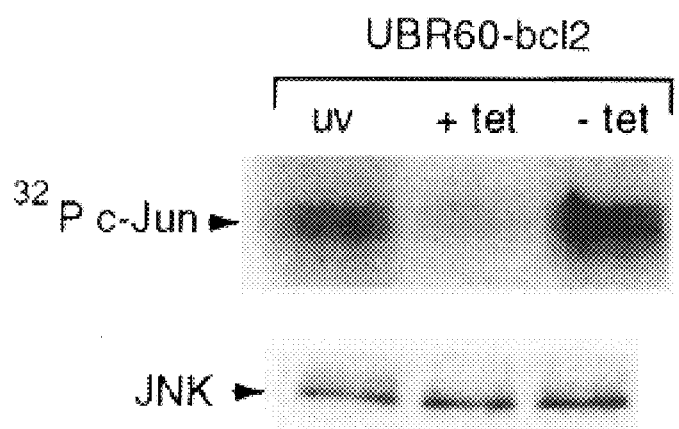
(FIG. 3A) Endogenous JNK/SAPK was immunoprecipitated from UBR60-bcl2 cells grown in the presence or absence (24 hrs) of tetracycline, and used to phosphorylate bacterially produced c-jun. Western blotting is shown to demonstrate comparable amounts of the immunoprecipitated kinase (JNK). For comparison, JNK/SAPK activity is shown following treatment of cells with uv-irradiation, the most potent known inducer of the stress kinase pathway.
Figure 3B:
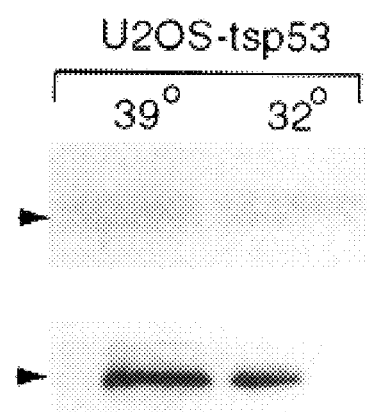
(FIG. 3B) Absence of JNK/SAPK activation associated with p53-mediated apoptosis. U2OS cells stably expressing a temperature-sensitive p53 (tsp53) were cultured for 18 hrs at the permissive temperature (32° C.). Marked apoptosis is observed after 24 hrs.
Figure 3C:
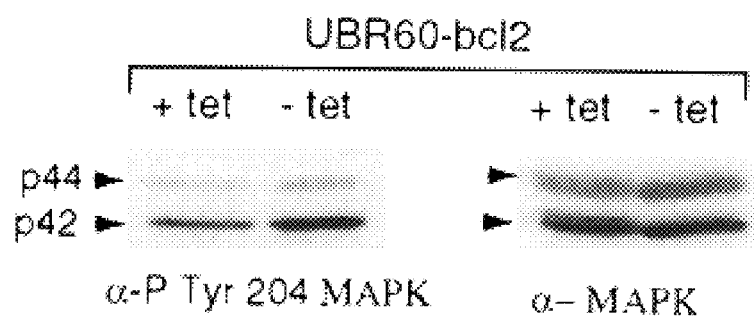
(FIG. 3C) Absence of BRCA1-mediated activation of the MAP kinase pathway. Western blot analysis of cellular lysates from UBR60-bcl2 cells, grown in the presence or absence (24 hrs) of tetracycline, using antibody against p42 and p44 MAK kinase (Erk1 and Erk2) and the catalytically activated, Fyr204 phosphorylated forms.
Figure 4A:
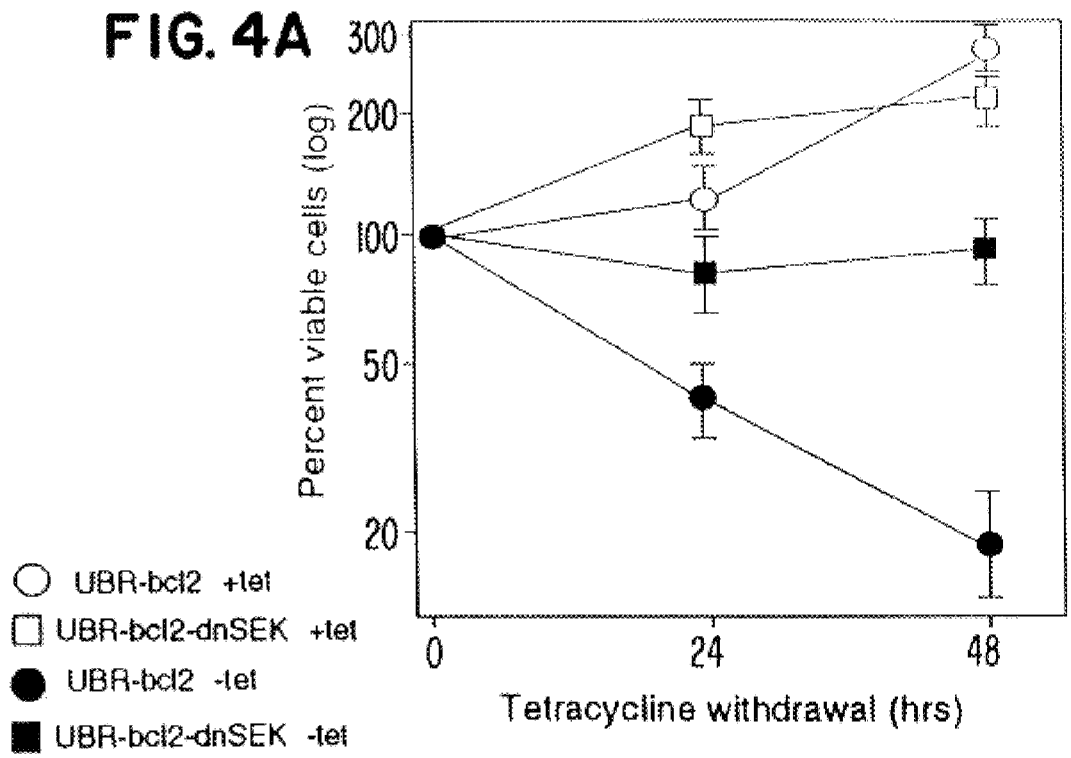
FIG. 4: Inhibition of BRCA1-mediated apoptosis by a dominant negative SEK1 mutant (FIG. 4A) Growth curve of UBR60-bcl2 cells and their derivatives with constitutive expression of the dominant negative SEK1 mutant (UBR60-bcl2-dnSEK cells), in the presence of tetracycline or following induction of BRCA1 expression. Viable cells were counted and standard deviations are given.
(FIG. 4B) Northern blot analysis of UBR60-bcl2 and UBR60-bcl2-dnSEK cells to demonstrate expression of endogenous SEK1 and the transfected dominant negative mutant (dnSEK1), unaltered inducible expression of BRCA1 and GADD45 in these two cell lines following tetracycline withdrawal. Loading control: GAPDH.
(FIG. 4C) Initiation of apoptosis in UBR60-bcl2 cells 48 hrs following tetracycline withdrawal, demonstrated by PARP cleavage and (FIG. 4D) Tunel assay. Expression of bcl2 in these cells delayed the onset of apoptosis, facilitating its demonstration.
(FIG. 4E) Delayed cell cycle progression following induction of BRCA1 in cells with constitutive expression of the dominant negative SEK1 mutant, demonstrated by FACS analysis of cells stained for DNA content using propidium iodide.
Figure 4B:
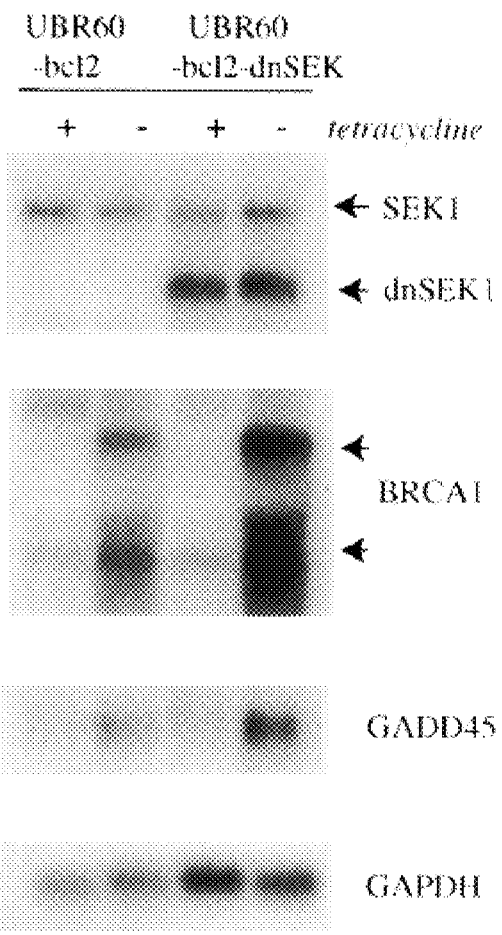
Figure 4C:
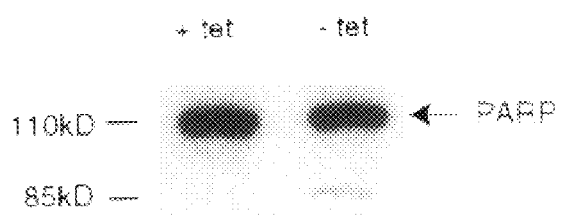
Figure 4D:

Induction of apoptosis in UBR60-bcl2 cells was first evident by PARP cleavage and Tunel staining 48 hrs following withdrawal of tetracycline (see FIG. 4C and D). To search for potential mechanisms involved in BRCA1-induced cell death, we analyzed the components of known apoptotic pathways in these cells, 24 hrs following induction of BRCA1. No changes were observed in the expression of endogenous p53, its target gene p21 (see below), or members of the bcl2 family, bax, bclx and bad (data not shown). However, consistent activation of JNK/SAPK was evident following induction of BRCA1 expression (FIG. 3A). Induction of BRCA1 led to increased kinase activity of endogenous JNK/SAPK, comparable to that observed following uv-irradiation, the most potent known inducer of JNK/SAPK (FIG. 3A). To confirm that activation of JNK/SAPK in U2OS cells was not universally observed following the triggering of apoptosis, we analyzed U2OS cells stably expressing a CMV-driven temperature-sensitive p53 allele (tsp53), which induces rapid cell death following switching to the permissive temperature (32° C.) (Michalovitz et al., 1990). No increase in JNK/SAPK activity was observed following overexpression of wild-type p53 (FIG. 3B). Also, induction of BRCA1 expression did not result in nonspecific activation of the MAP kinase pathway, as shown by the unaltered tyrosine phosphorylation of MAP kinase (ERK1 and ERK2) (FIG. 3C).

To determine whether activation of JNK/SAPK was required for BRCA1-mediated apoptosis, we stably transfected UBR60-bcl2 cells with a dominant negative mutant of SEKI, the common upstream regulator of JNK/SAPK family members (Sanchez et al., 1994; Yan et al., 1994; Derijard et 1., 1995). The resulting cells were called UBR60-bcl2-dnSEK. Constitutive expression of the dominant negative SEK1 mutant was demonstrated by northern blotting (FIG. 4B), and UBR60-bcl2-dnSEK cells displayed a growth rate identical to the parental UBR60-bcl2 cells in the presence of tetracycline (FIG. 4A), indicating that expression of the SEK1 mutant did not itself alter cellular proliferation. Inducible expression of BRCA1 was also unaltered in cells expressing the dominant negative SEK1 (FIG. 4B). Remarkably, however, induction of BRCA1 expression in these cells failed to trigger apoptosis (FIG. 4A). Disruption of JNK/SAPK signaling therefore antagonizes BRCA1-mediated cell death.

Example 4
Induction of a cellular senescence phenotype by BRCA1.

Figure 4E:
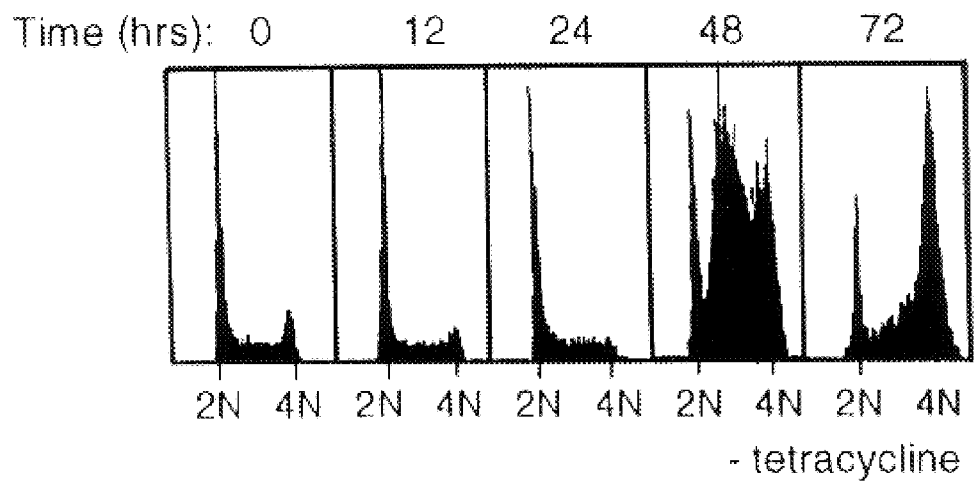
Figure 4E:
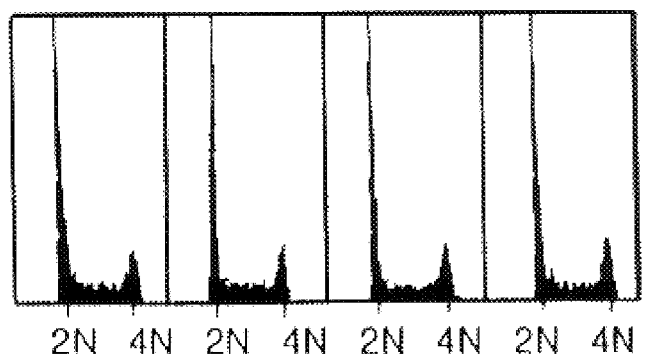

Prevention of BRCA1-mediated apoptosis by expression of the dominant negative SEK1 mutant uncovered a striking cellular proliferation defect (FIG. 4A). FACS analysis of UBR60-bcl2-dnSEK cells demonstrated an initial increase in G1 content, 24 hrs following induction of BRCA1 expression (FIG. 4E). This G1 arrest was overcome as cells slowly and synchronously progressed to S phase (48 hrs) and on to G2/M (72 hrs). U2OS cells are known to demonstrate a prominent G2/M arrest, in addition to the more typical G1 arrest, in response to inhibitors of cyclin-dependent kinases (van den Heuvel and Harlow, 1993). The BRCA1-induced prolongation of cell cycle progression was not accompanied by increased expression of genes associated with the G1 checkpoint (p53 and p21) or the G2/M checkpoint (14-3-3s; Hermeking et al, 1997) (data not shown). Remarkably, the cellular proliferation defect induced by BRCA1 was not reversible by readdition of tetracycline and suppression of BRCA1 expression. Cells expressing BRCA1 for 48 hrs failed to generate colonies upon withdrawal of BRCA1, indicating that this effect persisted beyond the expression of the gene itself (data not shown). Examination of cellular morphology revealed the presence of large cells, with abundant cytoplasm and multiple, well-demarcated nucleoli. Staining of BRCA1-expressing cells for endogenous b-galactosidase activity, a marker for cellular senescence (Dimri et al., 1995), was widely positive. Thus, following a marked prolongation in cell cycle transit, these cells demonstrate an irreversible proliferation defect, associated with large non-dividing cells that remain viable for prolonged periods in culture. Abrogation of JNK/SAPK-mediated cell death following inducible expression of BRCA1 therefore uncovers a phenotype that shares characteristic features of cellular senescence (Hayflick and Moorhead, 1961; Stein and Dulic, 1995).

Example 5
Gene expression profiling to identify BRCA1 targets

A potential role for BRCA1 in transcriptional regulation has been suggested by its ability to enhance transactivation of transiently transfected reporter constructs (Chapman and Verma, 1996; Monteiro, August and Hanafusa, 1996; Somasundaram et al., 1997; Ouichi et al., 1998; Zhang et al., 1998) and by its ability to interact with both RNA helicase (Scully et al., 1997a; Anderson et al., 1998) and the transcriptional repression cofactor CtIP (Yu et al., 1998). However, target genes whose expression is definitively regulated by BRCA1 remain unknown. Therefore, we searched for endogenous genes whose expression levels might be altered following inducible expression of BRCA1. Messenger RNA was isolated from UBR60-bcl2 cells at 6, 12, and 24 hrs following BRCA1 induction, biotinylated, and hybridized to high density oligonucleotide arrays representing 6,800 known transcripts and expressed sequence tags (Lockhart et al., 1996; Wodicka et al., 1997). A gene was considered a candidate BRCA1 target if is was progressively induced or repressed in at least two different time points following BRCA1 induction, and it exhibited an expression changes of at least 2-fold. To distinguish reproducible expression changes from those due to random biological variation, probes complementary to the candidate BRCA1 targets were used to screen northern blots containing total RNA derived from UBR60-bcl2 cells 24 hrs following BRCA1 induction.

Figure 5A:
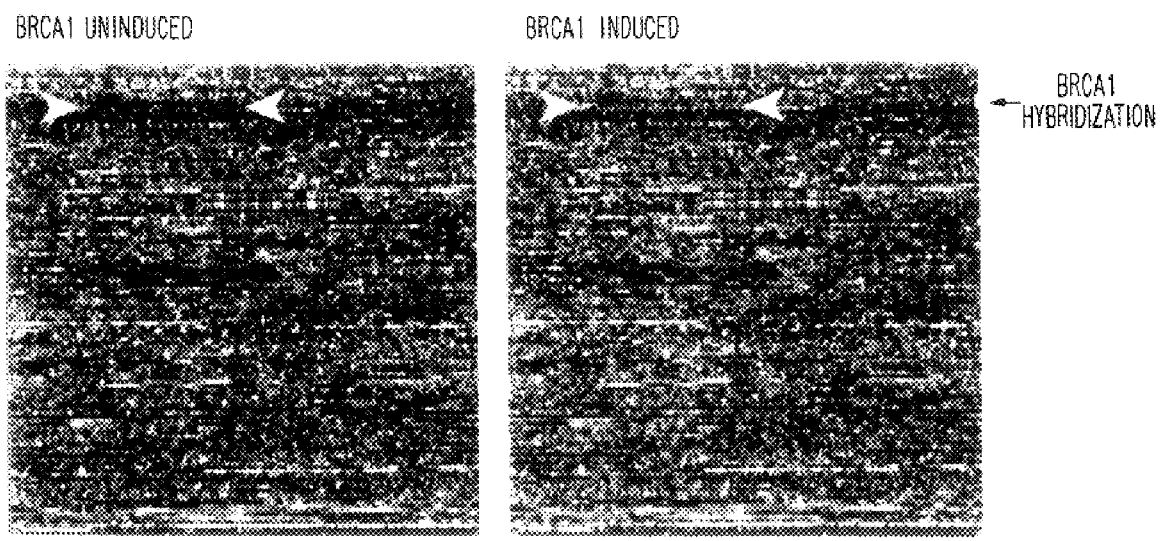
FIG. 5: Fluorescence images of oligonucleotide arrays hybridized with RNA from cells with inducible BRCA1 expression (FIG. 5A) Pseudocolored fluorescence images from two arrays of the same type hybridized with RNA from UBR60-bcl2 cells grown in the absence (left panel) or presence (right panel) of tetracycline (24 hrs). Color scheme ranges from blue (weakly hybridizing) to yellow and on to red (strongly hybridizing). The arrayed oligonucleotides complementary to BRCA1 itself are highlighted by yellow arrows.
(FIG. 5B) High-magnification fluorescence images of oligonucleotides complementary to BRCA1, GADD45 and EGR1 over a timecourse of BRCA1 induction (0 to 24 hrs following tetracycline withdrawal). "FC" indicates fold change in expression versus baseline (time point 0). Each panel displays five "perfect match" oligonucleotides (top row of each panel), which are complementary to the gene being interrogated, and five "mismatch" oligonucleotides (bottom row of each panel), which are identical to the perfect match oligonucleotides immediately above them, except for a single base difference at the central nucleotide position. The mismatch oligonucleotides serve as an internal control for hybridization specificity.
Figure 5B:
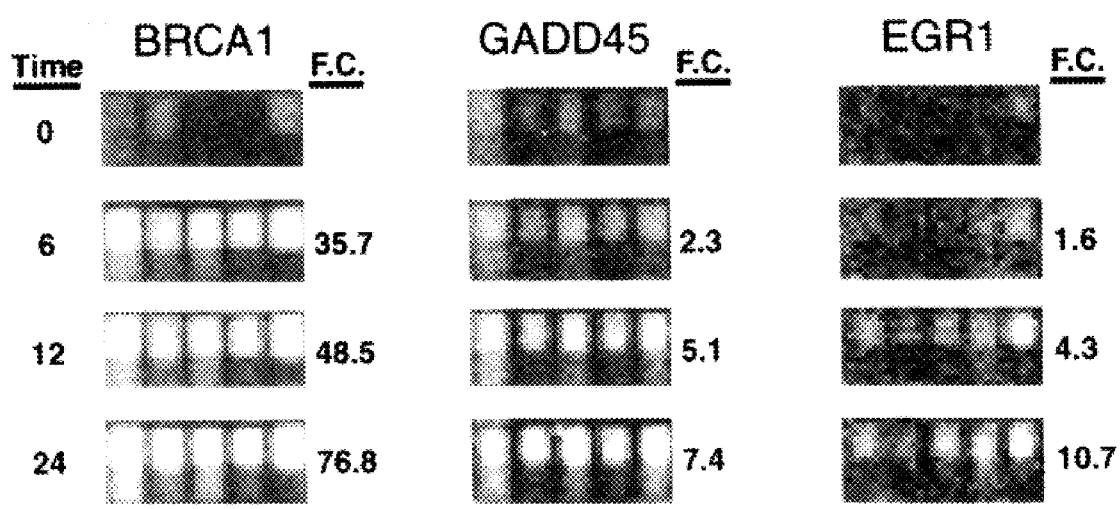
Figure 6B:
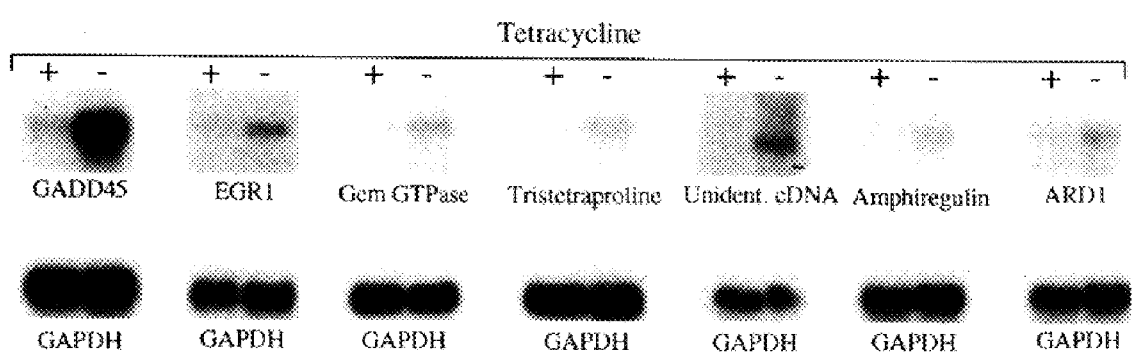
(FIG. 6B) Representative northern blots of candidate BRCA1 targets. Total cellular RNA from UBR60-bcl2 cells grown in the presence or absence (24 hrs) of tetracycline was analyzed using probes isolated from the candidate BRCA1 targets.

Potential BRCA1 targets identified by array hybridization experiments are listed in FIG. 5 and representative signals are shown in FIG. 6. BRCA1 mRNA itself was induced 72-fold at 24 hrs, a quantitative estimate consistent with that observed by Phosphorimager analysis of northern blots. Twenty three genes and ESTs identified as having increased expression following BRCA1 induction by array hybridization were confirmed as demonstrating at least 2-fold induction by northern blotting (FIG. 5). Only two genes were induced by at least 10-fold: the DNA damage-inducible gene GADD45 (35-fold) and the immediate early gene Early Growth Response 1 (EGR1) (10-fold). Oligonucleotide array hybridization also identified a small number of potential targets that were repressed following BRCA1 expression, but these could not be confirmed by northern blotting, since their baseline expression levels were below detection. However, two expression changes of possible interest were in the genes Ki-67 (12-fold repression) and prothymosin a (4-fold repression; data not shown). These genes have been previously implicated as possible prognostic markers in breast cancer, and Ki-67 expression in this tumor has been inversely correlated with that of BRCA1 (Tsitsiloni et al., 1993; Honkoop et al., 1998; Jarvis et al., 1998); although not detectable by northern blotting in U2OS cells, regulation of these genes by BRCA1 may be more evident in other cell types. In summary, of 6,800 genes and ESTs interrogated by array hybridization, we identified GADD45 and EGR1 as the two targets whose expression in U2OS cells was most dramatically altered following BRCA1 induction (FIG. 6). We analyzed these further to examine their potential relationship with the functional consequences of BRCA1 induction these cells.

Experimental Procedures: Oligonucleotide Array-based Expression Profiling

Messenger RNA was isolated from UBR60-bcl2 cells at 6, 12, and 24 hrs following BRCA1 induction. This RNA was amplified, labeled, and hybridized to oligonucleotide arrays as described (Lockhart et al., 1996; Wodicka et al., 1997). Each RNA sample was hybridized to a set of 5 arrays, which together enabled interrogation of the expression levels of 6,800 human genes and ESTs. Following quantitative expression analysis (Lockhart et al., 1996; Wodicka et al., 1997), a list of candidate BRCA1 targets was assembled by identifying genes that were progressively induced or repressed in at least two different time points and displayed an expression changes of at least two-fold.

Example 6
Induction of GADD45 by BRCA1

Figure 7A:
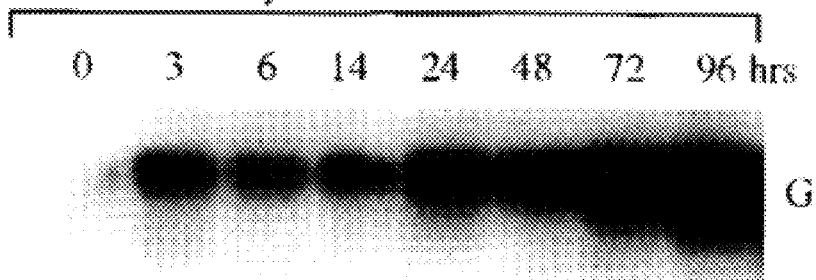
(FIG. 7A) Northern blot analysis of the time course of induction for GADD45 and EGR1 in UBR60-bcl2 cells, following withdrawal of tetracycline. The induction of BRCA1 (within 3 hrs) and GAPDH loading control are shown in FIG. 2B.
Figure 7B:
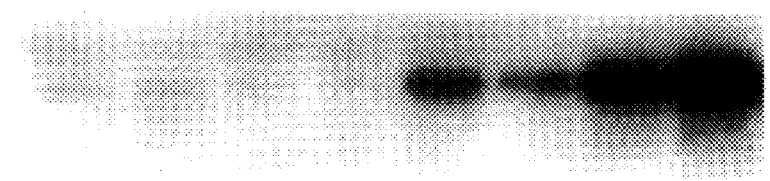
(FIG. 7B) Northern blot analysis, demonstrating the induction of GADD45 in U2OS cells following treatment with uv (20J/m2), IR (20Gy), or overexpression of p53 (growth of cells with ts p53 for 18 hrs at the permissive temperature, 32° C.), compared with induction of BRCA1 in UBR60-bcl2 cells.

GADD45 encodes a stress- and DNA damage-responsive gene, initially isolated by virtue of its induction following uv-irradiation and recently found to mediate the activation of JNK/SAPK by its upstream kinase MEK4 (also known as MAPKKK and MTK) (Fornace et al., 1988; Takekawa and Saito, 1998). Induction of GADD45 mRNA was virtually coincident with BRCA1 expression, detectable within 3 hrs of tetracycline withdrawal (FIG. 6C). Previous studies have demonstrated two distinct pathways of GADD45 induction: a p53 and ATM-dependent pathway that is triggered by IR (Kastan et al., 1992), and a p53-independent pathway initiated by treatment with uv irradiation or alkylating agents (so-called MUM stresses for Methyl methanesulfonate (MMS), Uv irradiation, and Medium starvation) (Fornace et al., 1989; Hollander et al., 1993; Zhan et al., 1994). The level of GADD45 induction by BRCA1 in U2OS cells was comparable to that induced by overexpression of wild-type p53 or IR (20 Gy) (FIG. 7A). To determine whether presence of endogenous p53 was required for BRCA1-mediated induction of GADD45, UBR60-bcl2 cells were stably transfected with HPV 16 E6 (resulting cells were called UBR60-bcl2-E6). Inactivation of endogenous p53 in these cells did not alter BRCA1-mediated induction of GADD45 (FIG. 7B). Thus, although both p53 and BRCA1 induce expression of GADD45, and BRCA1 has been reported to modulate the transcriptional activity of p53 in transient transfection assays, its induction of endogenous GADD45 is independent of p53.

Figure 7C:
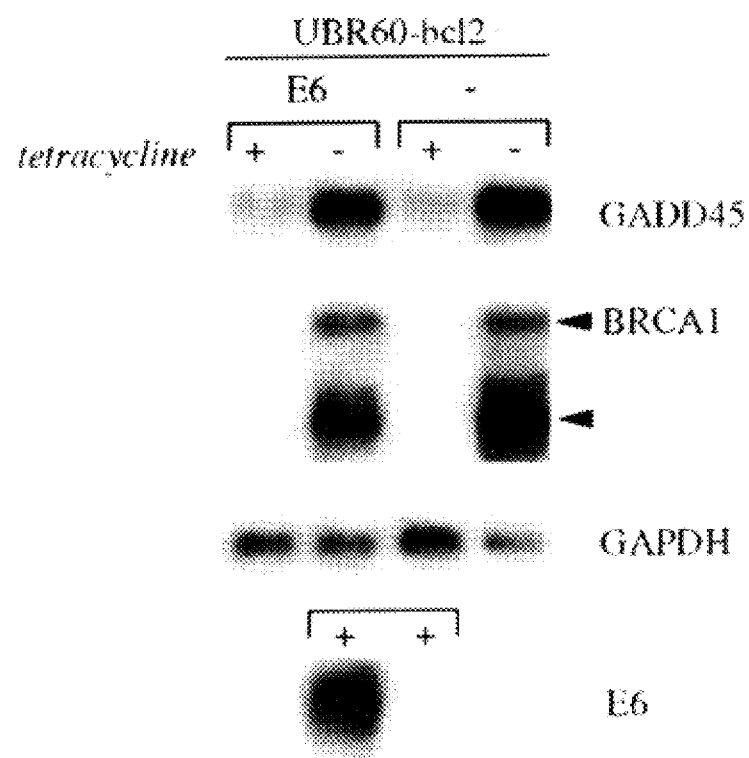
(FIG. 7C) p53-independent induction of GADD45 by BRCA1. Northern blot analysis of UBR60-bcl2-E6 cells grown in the presence or absence (24 hrs) of tetracycline, probed for BRCA1, GADD45, and GAPDH (loading control). Expression of the stably transfected HPV16E6 is demonstrated in the inset.
Figure 7D:
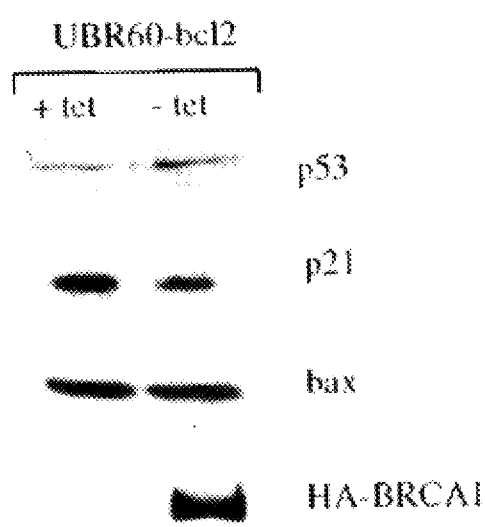
(FIG. 7D) Western blot showing unaltered expression of the p53 targets p21 and bax following induction of BRCA1 in UBR60-bcl2 cells. Baseline p53 was not detectable by immunoblotting, either in the presence or absence of BRCA1, and p53 levels were therefore analyzed following stabilization by uv-irradiation in the presence or absence of tetracycline.

In contrast to GADD45, we did not observe induction by BRCA1 of other known p53 target genes. Previous work has raised the paradoxical observations that BRCA1-null embryos have increased levels of p21 (Hakem et al., 1997; Ludwig et al., 1997), while transient transfection of BRCA1 itself leads to activation of the p21 promoter, potentially through both p53 dependent and independent pathways (Somasundaram et al., 1997; Ouichi et al., 1998; Zhang et al., 1998). However, no detectable alteration in the expression of either endogenous p53 or p21 transcripts was observed by northern blot analysis, nor were p53 or p21 protein levels altered by immunoblotting (FIG. 7C and data not shown). Other p53-target genes, including bax (FIG. 7C) and MDM2 (data not shown) were also unaffected by inducible expression of BRCA1. The potent induction of GADD45 by BRCA1 therefore is not associated with induction of other p53 target genes.

While GADD45 was the most highly induced BRCA1 target identified by hybridization to oligonucleotide arrays, a second transcript whose expression was significantly increased was EGR1. EGR1 encodes a serum-inducible zinc finger transcription factor, known to be induced following mitogenic stimulation and in response g-irradiation (Rubin et al., 1992). BRCA1 expression was not associated with induction of other immediate early genes, including C-MYC, C-FOS, C-JUN, JUN B or JUN D (data not shown), indicating that its induction of EGR1 was not the result of nonspecific mitogenic stimulation. In contrast to GADD45, EGR1 demonstrated a delayed time course of induction following expression of BRCA1 (FIG. 6C). Also, in contrast to GADD45 (FIG. 4B), the induction of EGR1 by BRCA1 was abrogated following expression of the dominant negative SEK1 mutant (data not shown). This suggests that BRCA1-mediated induction of EGR1 may be a consequence of the regulation by JNK/SAPK of known serum responsive elements within the EGR1 promoter (Changelian et al., 1989; Rubin et al., 1992).

By generating cell lines with tightly regulated inducible expression of BRCA1, we have identified downstream pathways that are likely to contribute to its function as a tumor suppressor. Induction of BRCA1 expression in osteosarcoma and in breast cancer cells triggers apoptosis. This effect is associated with activation of the JNK/SAPK stress response pathway, and it is abrogated by a dominant negative mutant of SEK1, known to inhibit JNK/SAPK signaling. Screening of oligonucleotide arrays to search for endogenous genes whose expression is regulated by BRCA1 identified the DNA damage-responsive gene GADD45 as a major downstream target gene for BRCA1. Of particular interest, while this manuscript was in preparation, Takekawa and Saito (1998) reported that GADD45 directly interacts with the upstream regulator of JNK/SAPK, MEKK4, leading to activation of JNK/SAPK signaling and apoptosis. Taken together, these observations suggest that BRCA1 may activate JNK/SAPK-dependent apoptosis through the induction of GADD45. These functional properties of BRCA1 are unaltered following inactivation of endogenous p53, another tumor suppressor implicated in the response to DNA damage, and previously implicated in transcriptional regulation by BRCA1. These results suggest a role for BRCA1 in the p53-independent cellular responses to DNA damage.

The primary phenotype observed following forced expression of wild-type BRCA1 is programmed cell death. This effect is so prompt that BRCA1 expression is detectable for only 24 hrs following withdrawal of tetracycline, whereupon cells expressing BRCA1 are lost from the culture and replaced with cells whose inducible promoter has been silenced through hypermethylation. The characterization of this cell death process as apoptotic is based on its abrogation by peptides that specifically inhibit the caspases required for apoptosis, as well as its delay by constitutive expression of the anti-apoptotic gene bcl2. PARP cleavage and Tunel staining, characteristics of cells undergoing apoptosis, are evident as the protective effect of bcl2 is overwhelmed. BRCA1-induced cell death appears to be mediated primarily through the JNK/SAPK stress response pathway. Signaling through JNK/SAPK is known to be triggered by uv-irradiation, osmotic stress and in response to cytokines and growth factors (Hibi et al., 1993; Derijard et al., 1994; Galcheva-Gargova et al., 1994; Kallunki et al., 1994; Kyriakis et al., 1994; Minden et al., 1994; Su et al., 1994; Rosette and Karin, 1996), and it has recently been implicated as a major apoptotic pathway following DNA damage and in response to Fas ligand and Tumor necrosis factor (TNF)-a (Xia et al., 1995; Verheij et al., 1996; Chen et al., 1996; Frisch et al, 1996, Latinis and Kokretzky, 1996; Wilson et al., 1996; Bossy-Wetzel et al., 1997; Fischer et al., 1997; Goillot et al., 1997).

Specific activation of JNK/SAPK by BRCA1 is comparable to that observed following uv-irradiation, the most potent inducer of this pathway, and BRCA1-mediated apoptosis is abrogated by expression of a dominant-negative mutant of the upstream kinase SEKI, which disrupts JNK/SAPK signaling. Our observation that BRCA1 induces expression of GADD45 provides a potential mechanism for its activation of JNK/SAPK-dependent apoptosis, given the very recent observation that GADD45 interacts with and activates the stress-responsive MTK1/MEK4 MAPKKK, an upstream regulator of JNK/SAPK, and that overexpression of GADD45 itself triggers apoptosis through JNK/SAPK signaling (Takekawa and Saito, 1998). Taken together, these observations suggest a BRCA1-mediated apoptotic pathway, involving components that have been implicated in the cellular response to DNA damage.

A second BRCA1-induced phenotype was uncovered following inhibition of JNK/SAPK signaling and suppression of apoptosis. This phenotype was characterized by grossly delayed cell cycle progression, culminating in the appearance of large cells with endogenous b-galactosidase activity, a marker for cellular senescence (Dimri et al., 1995). Consistent with cellular senescence, the induction of this large cell phenotype was not reversible following withdrawal of BRCA1 expression. Molecular mechanisms underlying senescence remain to be defined (Hayflick and Moorhead, 1961; Stein and Dulic, 1995), although this phenotype may be induced by loss of telomerase activity (Goldstein, 1990), expression of activated H-ras in primary cultured cells (Serrano et al., 1997), as well as by overexpression of the cyclin-dependent kinase inhibitor p16 INK4a (Alcorta et al., 1996; Hara et al., 1996). These genes are unlikely to contribute to the effect of BRCA1 in the cells studied here, since U2OS cells are immortal and have a homozygous deletion of p16-INK4a (data not shown).

The potential role of BRCA1 in transcriptional regulation has been suggested by the transactivational properties of its BRCA1 domain when fused to a heterologous DNA binding domain and its effect, with and without p53, on promoter reporters in transient transfection assays (Chapman and Verma, 1996; Monteiro, August and Hanafusa, 1996; Somasundaram et al., 1997; Ouichi et al., 1998; Zhang et al., 1998), as well as its potential associations with RNA helicase, the RNA polymerase 2 holoenzyme complex (Scully et al., 1997a; Anderson et al., 1998), and the transcriptional repression cofactor CtIP (Yu et al.,1998). Understanding the precise function of BRCA1 in transcriptional regulation would therefore benefit from the identification of native promoters that are regulated in a physiological context. Our analysis of gene expression profiles following BRCA1 induction allowed us to screen endogenous transcripts for 6,800 expressed sequences, leading to the identification of GADD45 and EGR1 as the major BRCA1 targets. The time course of EGR1 induction was delayed and it was abrogated in cells with disrupted JNK/SAPK signaling, suggesting an indirect consequence of BRCA1 expression. In contrast, GADD45 induction by BRCA1 was virtually immediate and it was unaffected by expression of the dominant negative SEK1 mutant.

GADD45 was first identified as a gene induced in response to DNA damage (Fornace et al., 1988), and its induction has served as a critical marker for ATM- and p53-dependent signaling following IR (Kastan et al., 1992). p53-independent activation of GADD45 , such as observed following induction of BRCA1, has also been noted following so-called MUM stress (Fornace et al., 1989; Hollander et al., 1993; Zhan et al., 1994). While the induction of GADD45 by p53 is thought to result from activation of a consensus p53 binding site within intron 3, the mechanism underlying its induction by MUM signals is less clearly defined. A GC-rich site within the GADD45 promoter is activated following treatment of cells with MMS, an effect that requires stable chromosomal integration of reporter constructs (Hollander et al., 1993; Zhan et al. 1998). We did not detect activation of the known GADD45 promoter sequence following either transient transfection or stable integration of reporter constructs into cells with inducible BRCA1 expression, suggesting that the BRCA1-responsive site may be located elsewhere (data not shown). Defining the mechanism by which BRCA1 induces expression of GADD45 will therefore require identification of this potential regulatory element and of transcription factors that may target that site. The scope of the invention should be determined not with reference to the above description, but should instead be determined with reference to the appended claims, along with the full scope of equivalents to which such claims are entitled.

REFERENCES

Alcorta, D. A., Xiong, Y., Phelps, D., Hannon, G., Beach, D., and Barrett, J. C. (1996) Involvement of the cyclin-dependent kinase inhibitor p16 (INK4a) in replicative senescence of normal human fibroblasts. Proc. Natl. Acad. Sci. USA 93, 13742–13747.

Anderson, S., Schlegel, B., Nakajima, T., Wolpin, E., and Parvin, J. (1998). BRCA1 protein is linked to the RNA polymerase II holoenzyme complex via RNA helicase A. Nature Genetics 19, 1–3.

Bossy-Wetzel, E., Bakiri, L, and Yaniv M. (1997) Induction of apoptosis by the transcription factor c-Jun EMBO J. 16, 1695–1709.

Cedar, H. (1988) DNA methylation and gene activity. Cell 53, 3–4.

Castilla, L. H., Couch, F. J., Erdos, M. R., Hoskins, K. F., Calzone, K., Garber, J. E., Boyd, J., Lubin, M. B>, Deshano, M. L., Brody L. C. (1994) Mutations in the BRCA1 gene in families with early-onset breast and ovarian cancer. Nature Genet. 8, 387–391.

Chapman, M. S. and Verma, I. M. (1996) Transcriptional activation by BRCA1. Nature (comment) 382, 678–679.

Changelian, P. S., Feng, P., King, T. C., and Milbrandt, J. (1989) Structure of the NGFI-A gene and detection of upstream sequences responsible for its transcriptional induction by nerve growth factor. Proc. Natl. Acad. Sci. USA 86. 377–381.

Chee, M., Yang, R., Hubbell, E., Berno, A., Huang, X. C., Stern, D., Winkler, J., Lockhart, D. J, Morris, M. S., and Fodor, S. P. (1996) Accessing genetic information with high-denisty DNA arrays. Sicence 274, 610–614.

Chen, Y. R., Wang, X., Templeton, D., Davis, R. J., and Tan, T. H. (1996) The role of c-Jun N-terminal kinase (JNK) in apoptosis induced by ultraviolet C and gamma radiation. Duration of JNK activation may determine cell death and proliferation. J. Biol. Chem. 271, 31929–31936.

Chen, J., Silver, D. P., Walpita, D., Cantor, S. B., Gazdar, A. F., Tomlinson, G., Couch, F. J., Weber, B. L., Ashley, T., Livingston, D. M., and Scully, R. (1998) Stable interaction between the products of the BRCA1 and BRCA2 tumor suppressor genes in mitotic and meiotic cells. Mol. Cell 2, 317–328.

Cho, R. J., Campbell, M. J., Winzeler, E. A., Steinmetz, L., Conway, A., Wodicka, L., Wolfsberg, T. G., Gabrielian, A. E., Landsman, D., Lockhart, D. J, and Davis, R. W. (1998). A genome-wide transcriptional analysis of the mitotic cell cycle. Mol. Cell 2, 65–73.

Derijard, B., Hibi, M., Wu, I H., Barrett, T., Su, B., Deng, T., Karin, M., and Davis, R. J. (1994) JNKI: a protein kinase stimulated by uv light and Ha-ras that binds and phosphorylates the c-Jun activation domain. Cell 76, 1025–1037.

Derijard, B., Raingeaud, J., Barrett, T., Wu, I -H., Han, J., Ulevitch, R. J., and Davis, R. J. (1995) Independent human MAP kinase signal transduction pathways defined by MEK and MKK isoforms Science 267, 682–685.

Dimri, G. P., Lee, X., Basile, G., Acosta, M., Scott, G., Roskelley, C., Medrano, E. E., Linskens, M., Rubelij, I., Pereira-Smith, O., et al. (1995) A biomarker that identifies senescent human cells in culture and in aging skin in vivo. Proc. Natl. Acad. Sci. USA 929 9363–9367.

El-Deiry, W. S., Tokino, T., Velculescu, V. E., Levy, D. B., Parsons, R., Trent, J. M., Lin, D., Mercer, E, Kinzler, K. W., and Vogelstein, B. (1993) WAF1, a potential mediator of p53 tumor suppression. Cell 75, 817–825.

Nishina, H., Fischer, K. D., Radvanyi, L., Shanhinian, A., Hakem, R., Rubie, E. A., Bernstein, A., Mak, T. W., Woodgett, J. R., and Penninger, J. M. (1997) Stress-signalling kinase Sek1 protects thymocytes from apoptosis mediated by CD95 and CD3. Nature 385, 350–353.

FitzGerald, M., MacDonald, D., Krainer, M., Hoover, I., O'Neil, E., Unsal, H., Silva- Arrieto, S., Finkelstein, D., Beer-Romero, P., Englert, C., Sgroi, D., Smith, B., Younger, J. W., Garber, J., Duda, R., Mayzel, K., Isselbacher, K., Friend, S., and Haber, D. A. (1996). Germ-line BRCA1 mutations in Jewish and non-Jewish women with early-onset breast cancer. New England Journal Medicine 334, 143–149.

Fornace Jr., A. J., Alamo, Jr, I., and Hollander, C.(1988) DNA damage-inducible transcripts in mammalian cells. Proc. Natl. Acad. Sci. USA 85, 8800–8804.

Fornace, Jr., A J., Nebert, D. W., Hollander, C., Luethy, J. D., Papathanasiou, M., Fargnoli, J, and Holbrook, N. J. (1989) Mammalian genes coordinately regulated by growth arrest signals and DNA damaging agents. Mol. and Cell. Biol. 9, 4196–4203.

Friedman, N. G., Ostermeyer, E. A., Szabo, C. I., Dowd, P., Lynch, E. D., Rowell, S. E., and King, M. C. (1994) Confirmation of BRCA1 by analysis of germline mutations linked to breast and voarian cancer in ten families. Nature Genet 8, 399–404.

Frisch, S., Vuaori, K., Kelaita, D., and Sicks, S. (1996) A role for Jun N-terminal kinase in anoikis: suppression by bc-12 and crmA J. Cell Biol. 135, 1377–1382.

Futreal, P., Liu, Q., Shattuck-Eidens, D., Cochran, C., Harshman, K., Tavtigian, S., Bennett, L., Haugen-Strano, A., Swensen, J., Miki, Y., Eddington, K., McClure, M., Frye, C., Weaver-Feldhaus, J., Ding, W., Gholami, Z., Soderkvist, P., Terry, L., Jhanwar, S., Berchuck, A., Iglehart, J., Marks, J., Ballinger, D., Barrett, J., Skolnick, M., Kamb, A., and Wiseman, R. (1994). BRCA1 mutations in primary breast and ovarian carcinomas. Science 266, 120–122.

Galcheva-Gargova, Z., Derijard, B., Wu, I -H., and Davis, R. J. (1994) An osmosensing signal transduction pathway in mammalian cells. Science 265, 806–808.

Goillot, E., Raingeaud, J., Ranger, Ann, Tepper, R. I., Davis, R. J., Harlow, E., and Sanchez, I. (1997) Mitogen-activated protein kinase-mediated Fas apoptotic signaling pathway. Proc. Natl. Acad. Sci. USA 94, 3302–3307.

Goldstein, S (1990). Replicative senescence: the human fibroblast comes of age. Science 249, 1129–1133.

Gossen , M and Bujard, H. (1992) Tight control of gene expression in mammalian cells by tetracylcline-responsive promoters. Proc. Natl. Acad. Sci USA 89, 5547–5551.

Gowen, L., Avrutskaya, A., Latour, A., Koller, B., and Leadon, S. (1998). BRCA1 required for transcription-coupled repair of oxidative DNA damage. Science, 1009–1012.

Gray, N. S., Wodicka, L., Thunnissen, A. M., Norman, T. C., Kwon, S., Espinoza, F. H., Morgan, D. O., Barnes, G., LeClerc, S., Meijer, L., Kim, S. H., Lockhart, D. J., and Schultz, P. G. (1998). Exploiting chemical libraries, structure, and genomics in the search for kinase inhibitors. Science 281, 533–538.

Hakem, R., de la Pompa, J. L., Sirard, C., Mo, R., Woo, M., Hakem, A., Wakeham, A., Potter, J., Reitmair, A., Billia, F., Firpo, E., Hui, C. C., Toberts, J., Rossant, J., and Mak, T. W. (1996). The tumor suppressor gene BRCA1 is required for embryonic cellular proliferation in the mouse. Cell 85, 1009–1023.

Hakem, R., de la Pompa, J., Elia, A., Potter, J., and Mak, T. (1997). Partial rescue of a BRCA1 5–6 early embryonic lethality by p53 or p21 null mutation. Nature Genet. 16, 298–302.

Hara, E., Smith, R., Parry, D., Tahara, H., Stone, S., and Peters, G. (1996). Regulation of p16 CDKN2 expression and its implications for cell immortalization and senescence. Mol. Cell. Biol. 16, 859–867.

Hayflick, L, and Moorhead, P. S. (1961). The serial cultivation of human diploid cell strains. Exp. Cell Res. 25, 585–621.

He, T. C., Sparks, A. B., Rago, C., Hermeking H., Zawel, L., da Costa, L. T., Morin, P. J., Vogelstein, B., Kinzler, K. W. (1998). Identification of c-myc as a target of the APC pathway. Science 281, 1509–1512.

Hermeking, H., Lengauer, C., Polyak, K., He, T. C., Zhang, L., Thiagalingam, S., Kinzler, K. W., and Vogelstein, B. (1997) 14-3-3 sigma is a p53-regulated inhibitor of G2/M progression. Mol Cell 1, 3–11.

Hibi, M., Lin, A., Smeal, T., Minden, A., and Karin, M.(1993) Identification of an oncoprotein-and uv-responsive kinase that binds and potentiates the c-Jun activation domain. Genes & Dev. 7, 2135–2148.

Hollander, M. C., Alamo, I., Jackman, J., Wang, M. G., McBride, O. W., and Fornace, Jr. A. J. (1993) Analysis of the mammalian gadd45 gene and its reponse to DNA damage. J. Biol. Chem. 268, 24385–24393.

Holt, J., Thompson, M., Szabo, C., Robinson-Benion, C., Arteaga, C., King, M. -C., and Jensen, R. (1996). Growth retardation and tumour inhibition by BRCA1. Nature Genet 12., 298–302.

Honkoop, A. H., van Diest, P. J., De Jong, J. S., Linn, S. C., Hoekman, G. G., Wagstaff, J., and Pinedo, H. M. (1998) Prognostic role of clinical, pathological and biological characteristics in patients with locally advanced breast cancer. Br. J. Cancer 77, 621–626.

Jarvis, E. M., Kirk, J. A., and Clark, C. L. (1998) Loss of nuclear BRCA1 expression in breast cancers is associated with a highly proliferative tumor phenotype. Cancer Genet. Cytogenet. 101, 109–115.

Kastan, M., Zhan, Q., El-Deiry, W., Carrier, F., Jacks, T., Walsh, W., Plunkett, B., Vogelstein, B., and Fornace, A. (1992). A mammalian cell cycle checkpoint pathway utilizing p53 and GADD45 is defective in ataxia-telangiectasia. Cell 71, 587–597.

Kallunki, T., Su, B., Tsigelny, I., Sluss, H. K., Derijard, B., Moore, G., Davis, R., and Karin, M. (1994) JNK2 contains a specificity-determining region responsible for efficient c-Jun binding and phosphorylation Genes & Dev. 8, 2996–3007.

Koonin, V. F., Altschul, S. F., and Bork, P. (1996). BRCA1 protein products: functional motifs. Nat. Genet. 13, 266–267.

Kyriakis, J. M., Banerjee, P., Nikolakaki, E., Dai, T., Rubie, E. A., Ahmad, M. F., Avruch, J., and Woodgett, R. R. (1994) The stress-activated protein kinase subfamily of c-Jun kinases Nature 369, 156–160.

Lane, T., Deng, C., Elson, A., Lyu, M., Kozak, C., and Leder, P. (1995). Expression of Brca1 is associated with terminal differentiation of ectodermally and mesodermally derived tissues in mice. Genes & Dev 9, 2712–2722.

Latinis, K. M., and Koretzky, G. A. (1996) Fas ligation induces apoptosis and Jun kinase activation independently of CD45 and Lck in human T cells Blood 87, 871–975.

Liu, C. Y., Fleshken-Nikitin, A., Li, S., Zeng, Y., and Lee, W. H.(1996) Inactivation of the mouse BRCA1 gene leads to failure in the morphogenesis of the egg cylinder in early postimplantation developmnent. Genes & Dev. 90, 2112–2143.

Lockhart, D. J., Dong, H., Byrne, M. C., Follettie, M. T., Gallo, M. V., Chee, M. S. et al. (1996). Expression monitoring by hybridization to high-density oligonucleotide arrays. Nature Biotechnology 14, 1675–1680.

Ludwig, T., Chapman, D. L., Papaioannou, V. E., and Efstratiadis, A. (1997) Targeted mutations of breast cancer susceptibility gene homologs in mice: lethal phenotypes of Brca1, Brca2, Brca1/Brca2, Brca1/p53, and Brca2/p53 nullizygous embryos. Genes & Dev 11, 1226–1241.

Marquis, S., Rajan, J., Wynshaw-Boris, A., Xu, J., and Yin, G. -Y. (1995). The developmental pattern of BRCA1 expression implies a role in differentiation of the breast and other tissues. Nat Genet 11, 17–28.

Michalovitz, D., Halevy, O., and Oren, M. (1990). Conditional inhibition of transformation and of cell proliferation by a temperature-sensitive mutant of p53. Cell 62, 671–680.

Miki, Y. et al (1994). A strong candidate for the breast and ovarian cancer susceptibility gene BRCA1. Science 266, 66–71.

Minden, A., Lin, A., Claret, F -X., Abo, A., and Karin, M.(1994) Differential activation of ERK and JNK mitogen-activated protein kinases by Raf-1 and MEKK. Science 266, 1719–1723.

Monteiro, A. N. A., August, A. and Hanafusa, H. (1996) Evidence for a transcriptional activation function of BRCA1 C-terminal region Proc. Natl. Acad. Sci. USA 93, 13595–13599.

Ouichi, T., Monteiro, A. N. A., August, A., Aaronson, S. A., and Hanafusa, H. (1998) BRCA1 regulates p53-dependent gene expression. Proc. Natl. Acad. Sci. USA 95, 2302–2306.

Patel, K. J., Vu, V. P., Lee, H., Corcoran, A., Thistlethwaite, F. C., Evans, M. J., Coiledge, W. H., Friedman, L. S., Ponder, B. A., and Venkitaraman, A. R. (1998). Involvement of Brca2 in DNA repair. Mol. Cell 1, 347–367.

Polyak, K., Xia, Y., Zweier, J. L., Kinzler, K. W., and Vogeistein, B. (1997) A model for p53-induced apoptosis. Nature 389, 300–305.

Rosette, C., and Karin, M. (1996) Ultraviolet light and osmotic stress: activation of the JNK cascade through multiple growth factor and cytokine receptors. Science 275, 1194–1197).

Rubin, D. R., Sukhatme, V., Qureshi, S., Hallahan, D., Weichselbaum, R. R., and Kufe, D. W. (1992) Ionizing radiation activates transcription of the EGR1 gene via CArG elements. Proc. Natl. Acad. Sci. USA 89, 10149–10153.

Ruffner, H. and Verma, I. M. (1997) BRCA1 is a cell cycle-regulated nuclear phosphoprotein. Proc. Natl. Acad. Sci. USA 94, 7138–7143.

Sanchez, I., Hughes, R. T., Mayer, B. J., Yee, K., Woodgett, J. R., Avruch, J., Kyriakis, J. M., and Zon, L. I. (1994) Role of SAPK/ERK kinase-1 in the stress-activated pathway regulating transcription factor c-Jun. Nature 372, 794–797.

Scully, R. S., Ganesan, S., Brown, M., Caprio, J. D., Cannistra, S., Feunteun, J., Schnitt, S., and Livingston, D. (1996). Location of BRCA1 in human breast and ovarian cell lines. Science 272, 123–25.

Scully, R. S., Anderson, S. F., Chao, D. M., Wei. W., Ye, L., Young, R. A., Livingston, D. M., and Parvin, J. D. (1997a) BRCA1 is a component of the RNA polymerase II holoenzyme. Proc. Nati. Acad. Sci. USA 94, 5605–5610.

Scully, R. S., Chen, J., Plug, A., Xiao, Y., Weaver, D., Feunteun, J., Ashley, T., and Livingston, D. (1997b). Association of BRCA1 with Rad51 in mitotic and meiotic cells. Cell 88, 265–75.

Scully, R. S., Chen, J., Ochs, R. L, Keegan, K., Hoekstra, M., Feunteun, J., and Livingston, D. M. (1997c). Dynamic gahnges of BRCA1 subnuclear location and phosphorylation state are initiated by DNA damage. Cell 90, 425–435.

Serrano, M., Lin, A. W., McCurrach, M. E., Beach, D., and Lowe, S. W. (1997), Oncogenic ras provokes premature cell senescence associated with accumulation of p53 and p16INK4a. Cell 88, 593–602.

Shao, N., Chai, Y., Shyam, E., Reddy, P., and Rao, V. (1996). Induction of apoptosis by the tumor suppressor protein BRCA1. Oncogene 13, 1–7.

Shattuck-Eidens, D., McCure, M., Simard, J., Labne, F., Narod, S., Couch, F., Hoskins, K., Weber, B., Castilla, L., Erdos, M., Brody, L., Friedman, L., Ostermeyer, E., Szabo, C., King, M. -C., Jhanwar, S., Offit, K., Norton, L., Gilewski, T., Lubin, M., Osborne, M., Black, D., Boyd, M., Steel, M., Ingles, S., Haile, R., Lindbloom, A., Olsson, H., Borg, A., Bishop, D., Solomon, E., Radice, P., Spatti, G., Gayther, S., Ponder, B., Warren, W., Stratton, M., Liu, Q., Fujimura, F., Lewis, C., Skolnick, M., and Goldgar, D. (1995). A collaborative survey of 80 mutations in the BRCA1 breast and ovarian cancer susceptibility gene. JAMA 273, 535–541.

Shin, T. H., Paterson, A. J., Grant III, J. H., Meluch, A. A., and Kudlow, J. E. (1992). 5-azacytidine treatment of HA-A melanoma cells induces SpI activity and concomitant transforming growth factor a expression. Mol and Cell Biol 12. 3998–4006.

Simard, J., Tonin, P., Durocher, F., Morgan, K., Rommens, J., Gingras, S., Samson, C., Leblanc, J. F., Belanger, C., Dion, F. (1994) Common origins of BRCA1 mutations in Canadian breast and ovarian cancer families. Nature Genet 8, 392–398.

Somasundaram, K., Zhang, H., Zeng, Y -X, Houvras, Y., Peng, Y., Zhang, H., Wu, G. S., Licht, J. D., Weber, B. L., and El-Deiry, W. S. (1997) Arrest of the cell cycle by the tumour-suppressor BRCA1 requires the CDK-inhibityor p21 WAF1/CIP1 Nature 389, 187–190.

Southern, E. M. (1996) DNA chips: analysing sequence by hybridization to oligonucleoties on a large scale. Trends in Genet 12, 110–115.

Stein, G. H., and Dulic, V. (1995). Origins of G1 arrest in senescent human fibroblasts. Bioessays 17, 537–543.

Su, B., Jacinto, E., Hibi, M., Kalunki, T., Karin, M., and Ben-Neriah, Y. (1994) JNK is involved in signal integration during costimulation of T lymphocytes. Cell 77, 727–736.

Takekawa, M., and Saito, H. (1998) A family of stress-inducible GADD45-like proteins mediate activation of the stress-responsive MTK1/MEKK4 MAPKKK Cell 95, 521–530.

Thakur, S., Zhang, H., Peng, Y., Le, H., Carroll, B., Ward, T., Eao, J., Farid, L., Couch, F., Wilson, R., and Weber, B. (1997). Localization of BRCA1 and a splice variant identifies the nuclear localization signal. Mol. Cell. Biol. 17, 444–452.

Thomas, J. E., Smith, M. Tonkinson, J. L., Rubinfeld, B. and Polakis, P. (1997) Induction of phosphorylation on BRCA1 during the cell cycle and after DNA damage. Cell Growth Differ 8, 801–809.

Thornberry, N. A., and Lazebnik, Y. (1998) Caspases: enemies within. Science 281, 1312–1316.

Tsitsiloni, O. E., Stiakakis, J., Koutselinis, A., Gogas, J., Markopoulos, C., Yiaiouris, P., Bekris, S., Panoussopoulos, D., Kortsis, V., Voelter, W., and Haritos, A. A. (1993) Expression of alpha-thymosins in human tissues in normal and abnormal growth. Proc. Natl. Acad. Sci. USA 90, 9504–9507.

van den Heuvel, S., and Harlow, E. (1993) Distinct roles for cyclin-dependent kinases in cell cycle control. Science 262, 2050–2054.

Velculescu, V. E., Zhang, L., Vogelstein, B., and Kinzler, K. W. (1995) Serial analysis of gene expression. Science 270, 484–487.

Verheij. M., Bose, R., Lin, X. H., Yao, B., Jarvis, W. D., Grant, S., Birrer, M. J., Szabo, E., Zon, L. I., Kyriakis, J. M., Haimovitz-Friedman, A., Fuks, Z., and Kolesnick, R. N. (1996) Requirement for ceramide-initiated SAPK/JNK signalling in stress- induced apoptosis. Nature 380, 75–79.

Westphal, C. H., Rowan, S., Schmaltz, C., Elson, A., Fisher, D. E., and Leder, P. Atm and p53 cooperate in apoptosis and suppression of tumorigenesis, but not in resistance to acute radiation toxicity. Nature Genet. 16, 397–401 (1997a)

Westphal, C. H., Schmaltz, C., Rowan, S., Elson, A., Fisher, D. E., and Leder, P. (1997b). Genetic interactions between atm and p53 influence cellular proliferation and irradiation-induced cell cycle checkoints. Cancer Res. 57, 1664–1667.

Wilson, C. A., Payton, M. N., Pekar, S. K., Zhang, K., Pacifici, R. E., Gudas, J. L., Thukral, S., Calzone, F. J., Reese, D. M., and Slamon, D. I. (1996) BRCA1 protein products: antibody specificity . . . Nature Genet. (correspondence) 13, 264–265.

Wilson, D. J., Fortner, K. A., Lynch, D. H., Mattingly, R. R., MAcara, I. G., Posada, J. A., and Budd, R. C. (1996) JNK, but not MAPK, activation is associated with Fas-mediated apoptosis in human T cells. Eur. J. Immunol 26, 989–994.

Wilson, C., Payton, M., Elliott, G., Buaas, F., Cajulis, E., Grosshans, C., Ramos, L., Reese, D., Slamon, D., and Calzone, F. (1997). Differential subcellular localization, expression and biological toxicity of BRCA1 and the splice variant BRCA1-D11b. Oncogene 14, 1–16.

Wodicka, L., Dong, H., Mittmann, M., Ho, M. H., and Lockhart, D. J. (1997) Genome-wide expression monitoring in Saccharomyces cerevisiae. Nature Biotechnol. 15, 1359–1367.

Wu, L., Wang, Z., Tsan, J., Spillman, M., Phung, A., Xu, X., Yang, M., Bowcock, L. H. A., and Baer, R. (1996). Identification of a RING protein that can interact in vivo with the BRCA1 gene product. Nat Genet 14, 430–40.

Xia, Z., Dickens, M., Raingeaud, J., Davis, R. J., and Greenberg, M. E. (1995) Opposing effects of ERK and JNK-p38 MAP kinases on apoptosis. Science 270, 1326–1331.

Yan, M., Dai, T., Deak, J. C., Kyriakis, J. M., Zon, L. I., Woodgett, J. R., and Templeton, D. J. (1994) Activation of stress-activated protein kinase by MEKKI phosphorylation of its activator SEKI. Nature 372, 798–800.

Yu, X., Wu, L. C., Bowcock, A. M., Aronheim, A., and Baer, R. (1998) The C-terminal (BRCT) domains of BRCA1 interact in vivo with CtIP, a protein implicated in the CtBP pathway of transcriptional repression. J. Biol. Chem. 273, 25388–25392.

Zhan, Q., Bae, I., Kastan, M. B., and Fornace, Jr. A. J. (1994) The p53-dependent g-ray response of GADD45. Cancer Res. 54, 2755–2760.

Zhan, Q., Chen, I -T., Antinore, M. J., and Fornace Jr, A. J. (1998). Tumor suppressor p53 can participate in transcriptional induction of the GADD45 promoter in the absence of direct DNA binding. Mol. Cell. Biol. 18, 2768–2778.

Zhang, H., Somasundaram, K., Peng, Y., Tian, H., Zhang, H., Bi, D., Weber, B. L., and El-Deiry, W. S. (1998) BRCA1 physically associates with p53 and stimulates its transcriptional activity. Oncogene 16, 1713–1721.

What is claimed is:

1. A method for detecting a BRCA1 gene functional mutation in target cells comprising the steps of:

detecting expression of a plurality of down-stream genes of BRCA1 in a sample of (a) target cells and (b) reference cells having a wild-type BRCA1 gene, the reference cells being otherwise substantially similar to the target cells, the down-stream genes being up- or down-regulated by the wild-type BRCA1 gene, wherein said down-stream genes comprise at least one BRCA1 up-regulated gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA00027, and Nucleotide binding protein, or at least one BRCA1 down-regulated gene selected from the group consisting of Pim-1, Pigf, GF14Ω, Mki67a and prothymosin-α; and comparing the expression of the down-stream genes in the target cells and the reference cells, wherein a difference in the expression between the target cells and reference cells suggests a BRCA1 functional mutation in the target cells.

2. The method of claim 1, wherein said down-stream genes are transcriptionally regulated by said wild-type BRCA1 gene and the expression of said down-stream genes is detected by measuring amounts of transcripts of said down-stream genes in said reference and target cells.

3. The method of claim 2, wherein said amounts of transcripts are measured with high density nucleic acid array.

4. The method of claim 1, wherein said down-stream genes comprise at least one BRCA1 up-regulated gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, and Nucleotide binding protein.

5. The method of claim 1 wherein said down-stream genes comprise at least one BRCA1 down-regulated gene selected from the group consisting of Pim-1, Pigf, and GF14Ω.

6. The method of claim 1 wherein said down-stream genes comprise at least one BRCA1 down-regulated gene selected from the group consisting of Mki67a and prothymosin-α.

7. The method of claim 1 further comprising the step of: indicating a loss of function mutation in the BRCA1 gene in the target cells if the expression of said BRCA1 up-regulated genes is at least two times less in said target cells than in said reference cells or if the expression of said BRCA1 down-regulated genes is at least two times more in said target cells than in said reference cells.

8. An in-cell functional assay for a BRCA1 sequence alteration comprising the steps of:
    detecting expression of a plurality of BRCA1 down-stream genes in a target sample from target cells having a BRCA1 sequence alteration and in a reference sample from reference cells having a wild-type BRCA1 gene, said reference cells being otherwise substantially similar to said target cells, said down-stream genes being up- or down-regulated by said wild-type BRCA1 gene, wherein said down-stream genes comprise at least one BRCA1 up-regulated gene selected from the group consisting of gadd45, histone H4, EGR1, ATF3, Jun-B, Rev-Erb α, Etr101m A20, tristetraproline (TTP) Germ GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, and Nucleotide binding, or at least one BRCA1 down-regulated gene selected from the group of Pim-1, Pigf, GF14Ω, Mki67a and prothymosin-α; and
    comparing and expression in said target sample to said expression in said reference sample, wherein a difference in the expression between said two samples suggests that said BRCA1 sequence alteration affects the biological function of BRCA1.

9. The method of claim 8, wherein said down-stream genes are transcriptionally regulated by said wild-type BRCA1 gene and the expression of said down-stream genes is detected by measuring amounts of transcripts of said down-stream genes in said reference and target cells.

10. The method of claim 9, wherein said amounts of transcripts are measured with a high density nucleic acid array.

11. The method of claim 8 wherein said down-stream genes comprise at least one BRCA1 up-regulated gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, and Nucleotide binding protein.

12. The method of claim 8 wherein said down-stream genes comprise at least one BRCA1 down-regulated gene selected from the group consisting of Pim-1, Pigf, and GF14Ω.

13. The method of claim 8 wherein said down-stream genes comprise at least one BRCA1 down-regulated gene selected from the group consisting of Mki67a and prothymosin-α.

14. The method of claim 8 further comprising the steps of:
    indicating that said BRCA1 sequence alteration is a loss of wild-type function mutation if the expression of said BRCA1 up regulated genes is at least two times less in said target cells than in said reference cells or if the expression of said BRCA1 down regulated genes is at least two times more in said target cells than in said reference cells.

15. A method for detecting a mutation in a target BRCA1 gene using a computer comprising:
    inputting wild-type expression data of a plurality of down-stream genes in a wild-type sample containing a wild-type BRCA1 gene, said down-stream genes being transcriptionally regulated by said wild-type BRCA1 gene, wherein said down-stream genes comprise at least one BRCA1 up-regulated gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, and Nucleotide binding protein, or at least one BRCA1 down-regulated genie selected from the group consisting of Pim-1, Pigf, GF14Ω, Mki67a and prothymosin-α;
    inputting target expression data of said plurality of down-stream genes in a target sample containing said target BRCA1 gene;
    comparing the target and wild-type expresssion data to determine differences, wherein differences suggest a mutation in said target BRCA1 gene.

16. The method of claim 15 wherein said down-stream genes comprise at least one BRCA1 up-regulated gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, and Nucleotide binding protein.

17. The method of claim 15 wherein said down-stream genes comprise at least one BRCA1 down-regulated gene selected from the group consisting of Pim-1, Pigf, and GF14Ω.

18. The method of claim 15 wherein said down-stream genes comprise at least one BRCA1 down-regulated gene selected from the group consisting of Mki67a and prothymosin-α.

19. The method of claim 15 further comprising the step of:
indicating a mutation in said target BRCA1 gene if the expression of said BRCA1 up-regulated genes is at least two times less in said target cells than in said reference cells or if the expression of said BRCA1 down-regulated genes is at least two times more in said target cells than in said reference cells.

20. A method of identifying anti-cancer drugs, comprising the step of:
contacting a test compound with a human cell;
monitoring expression of a plurality of BRCA1-downstream genes, wherein said genes which are activated by or repressed by BRCA1 comprise at least one gene selected from the group consisting of gadd45, histone H4, EGR1, ATF3, Jun-B, Rev-Erb α, Etr101A20, tristetraproline(TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, and Nucleotide binding protein, or at least one BRCA1 down-regulated gene selected from the group consisting of Pigf, GF14Ω, and Mki67a;
identifying a test compound as a potential anti-cancer drug if it increases expression of a BRCA1 up-regulated gene or decreases expression of a BRCA1 down-regulated gene in the human cell.

21. The method of claim 20 wherein the cell is a breast cancer cell.

22. The method of claim 20 wherein the cell is a tumor cell.

23. The method of claim 20 wherein the cell contains no wild-type BRCA1 genes.

24. The method of claim 20, wherein the expression of said BRCA1 up-regulated and down-regulated genes is detected by measuring amounts of transcripts of said genes in said cell.

25. The method of claim 24, wherein said amounts of transcripts are measured using a high density nucleic acid array.

26. The method of claim 20 wherein said down-stream genes comprise at least one BRCA1 up-regulated gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, and Nucleotide binding protein.

27. The method of claim 20 wherein said down-stream genes comprise at least one BRCA1 down-regulated gene selected from the group consisting of Pim-1, Pigf, and GF14Ω.

28. The method of claim 20 wherein said downstream gene is Mki67a.

29. A method for detecting a BRCA1 gene functional mutation in target cells comprising the steps of:
detecting expression of a down-stream gene of BRCA1 in a sample of (a) target cells, and (b) reference cells having a wild-type BRCA1 gene, said reference cells being otherwise substantially similar to said target cells, said down-stream gene being selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α; and
comparing the expression of said down-stream gene in said target cells and said reference cells, wherein a difference in said expression between the target cells and reference cells suggests a BRCA1 functional mutation in the target cells.

30. An in-cell functional assay for a BRCA1 sequence alteration comprising the steps of:
detecting expression of a down-stream BRCA1-regulated gene selected from the group consisting of gadd45, histone H4, EGR1, ATF3, Jun-B, Rev-Erb a, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α, in a target sample from target cells having a BRCA1 sequence alteration and in a reference sample from reference cells having a wild-type BRCA1 gene, said reference cells being otherwise substantially similar to said target cells; and
comparing said expression in said target sample to said expression in said reference sample, wherein a difference in the expression between said two samples suggests that said BRCA1 sequence alteration affects the biological function of BRCA1.

31. A method for detecting a mutation in a target BRCA1 gene using a computer comprising:
inputting wild-type expression data of a down-stream gene in a wild-type sample containing a wild-type BRCA1 gene, said down-stream gene being transcriptionally regulated by said wild-type BRCA1 gene, said down-stream gene being selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pim-1, Pigf, GF14Ω, Mki67a and prothymosin-α;
inputting target expression data of said down-stream gene in a target sample containing said target BRCA1 gene;
comparing the target and wild-type expresssion data to determine differences, wherein differences suggest a mutation in said target BRCA1 gene.

32. A method of identifying anti-cancer drugs, comprising the step of:
contacting a test compound with a human cell;
monitoring expression of a BRCA1-downstream gene selected from the group consisting of gadd45, histone H4, EGR1, ATF3, Jun-B, Rev-Erb α, Etr101, A20, tristetraproline (TTP), Gem GTPase, Br140, R12810, PM-sc175, ARD1, hepatic leukemia factor, amphiregulin, TR3, orphan receptor (NAK1), fibroblast activating protein-α, IL4 receptor α, R41997, H81220, KIAAA0027, Nucleotide binding protein, Pigf, GF14Ω, and Mki67a and prothymosin-α;
identifying a test compound as a potential anti-cancer drug if it increases expression of a BRCA1 up-regulated gene or decreases expression of a BRCA1 down-regulated gene in the human cell.

* * * * *

UNITED STATES PATENT AND TRADEMARK OFFICE
CERTIFICATE OF CORRECTION

PATENT NO. : 6,258,536 B1
DATED : July 10, 2001
INVENTOR(S) : Jonathan Oliner et al.

Page 1 of 1

It is certified that error appears in the above-identified patent and that said Letters Patent is hereby corrected as shown below:

Column 43, claim 8,
Line 55, "Etr101m A20" has been replaced with -- Etr101, A20 --, and "Germ" has been replaced with -- Gem --,
Line 60, -- protein -- has been inserted after "binding",
Line 61, -- consisting -- has been inserted after "group",
Line 63, "and" has been replaced with -- said --.

Column 44, claim 15,
Line 47, "genie" has been replaced with -- gene --.

Column 45, claim 20,
Line 20, "Etr101A20" has been replaced with -- Etr101, A20 --.

Column 45, claim 27,
Line 54, "Pim-1" has been deleted.

Column 46, claim 32,
Line 61, "and prothymosin-α" has been deleted.

Signed and Sealed this

Twelfth Day of March, 2002

Attest:

Attesting Officer

JAMES E. ROGAN
Director of the United States Patent and Trademark Office